(12) United States Patent
Minami

(10) Patent No.: US 12,018,280 B2
(45) Date of Patent: Jun. 25, 2024

(54) METHOD FOR FREEZING AGGREGATES OF PLURIPOTENT STEM CELL-DERIVED CARDIOMYOCYTES

(71) Applicant: KYOTO UNIVERSITY, Kyoto (JP)

(72) Inventor: Itsunari Minami, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 364 days.

(21) Appl. No.: 16/084,132

(22) PCT Filed: Mar. 17, 2017

(86) PCT No.: PCT/JP2017/010972
§ 371 (c)(1),
(2) Date: Sep. 11, 2018

(87) PCT Pub. No.: WO2017/159862
PCT Pub. Date: Sep. 21, 2017

(65) Prior Publication Data
US 2020/0325448 A1    Oct. 15, 2020

(30) Foreign Application Priority Data

Mar. 18, 2016  (JP) ................................. 2016-055913

(51) Int. Cl.
| | | |
|---|---|---|
| C12N 5/077 | (2010.01) | |
| A01N 1/02 | (2006.01) | |
| A61K 35/34 | (2015.01) | |
| G01N 33/50 | (2006.01) | |

(52) U.S. Cl.
CPC .......... *C12N 5/0657* (2013.01); *A01N 1/0221* (2013.01); *A61K 35/34* (2013.01); *G01N 33/5061* (2013.01); *C12N 2500/30* (2013.01); *C12N 2500/32* (2013.01); *C12N 2500/34* (2013.01); *C12N 2501/415* (2013.01); *C12N 2501/999* (2013.01); *C12N 2506/45* (2013.01)

(58) Field of Classification Search
CPC ................................................. C12N 5/0657
See application file for complete search history.

(56) References Cited

U.S. PATENT DOCUMENTS

| | | |
|---|---|---|
| 8,658,425 B2 | 2/2014 | Nakatsuji et al. |
| 9,109,205 B2 | 8/2015 | Hattori et al. |
| 9,499,790 B2 | 11/2016 | Nakatsuji et al. |
| 9,587,220 B2 | 3/2017 | Nakatsuji et al. |
| 10,233,426 B2 | 3/2019 | Nakatsuji et al. |
| 10,426,802 B2 | 10/2019 | Sakamoto et al. |
| 2010/0189699 A1 | 7/2010 | Hattori et al. |
| 2013/0183753 A1 | 7/2013 | Nakatsuji et al. |
| 2014/0127807 A1 | 5/2014 | Nakatsuji et al. |
| 2015/0017718 A1 | 1/2015 | Nakatsuji et al. |
| 2015/0366918 A1 | 12/2015 | Hattori et al. |
| 2016/0002600 A1 | 1/2016 | Nakatsuji et al. |
| 2016/0067284 A1 | 3/2016 | Sakamoto et al. |
| 2017/0152485 A1 | 6/2017 | Nakatsuji et al. |
| 2018/0153155 A1 | 6/2018 | Ohashi et al. |

FOREIGN PATENT DOCUMENTS

| | | | |
|---|---|---|---|
| JP | 2014-183825 A | 10/2014 | |
| WO | 2009/017254 A1 | 2/2009 | |
| WO | 2012/026491 A1 | 3/2012 | |
| WO | 2013/111875 A1 | 8/2013 | |
| WO | 2014/136519 A1 | 9/2014 | |
| WO | 2014/185517 A1 | 11/2014 | |
| WO | 2015/037706 A1 | 3/2015 | |
| WO | WO-2015146631 A1 * | 10/2015 | ........... C12N 5/0658 |
| WO | 2015/182765 A1 | 12/2015 | |
| WO | WO-2015182765 A1 * | 12/2015 | ........... C12N 5/0657 |
| WO | 2017010544 A1 | 1/2017 | |

OTHER PUBLICATIONS

Okawara et al. (Feb. 1, 2016, J. Japanese Society for Regenerative Med., vol. 15, p. 257). (Year: 2016).*
Xu et al. (2011, Regen. Med. vol. 6(1), pp. 53-66) (Year: 2011).*
Ha et al. (2005, Human Reproduction, vol. 20(7), pp. 1779-1785) (Year: 2005).*
Kaestner et al. (2014, Circulation Res., pp. 1623-1639). (Year: 2014).*
BioLife Solutions Product Information Sheet (Year: 2015).*
English Translation of WO 2015/146631 (Year: 2015).*
English Translation of WO 2015/182765 A1 (Year: 2015).*
International Search Report and Written Opinion issued in connection with International Patent Application No. PCT/JP2017/010972, dated Jun. 6, 2017. (10 pages).
Paul W. Burridge et al: "Chemically Defined Culture and Cardiomyocyte Differentiation of Human Pluripotent Stem Cells" In: "Current Protocols in Human Genetics", Oct. 6, 2015, XP055290930, pp. 21.3.1-21.3.15.
Cláudia Correia et al: Effective Hypothermic Storage of Human Pluripotent Stem Cell-Derived Cardiomyocytes Compatible With Global Distribution of Cells for Clinical Applications and Toxicology Testing, Stem Cells Translational Medicine, vol. 5, No. 5, Mar. 29, 2016, pp. 658-669, XP055605731.
Marcela K. Preininger et al: "Cryopreservation of Human Pluripotent Stem Cell-Derived Cardiomyocytes: Strategies, Challenges, and Future Directions" In: "Advances in Mitochondrial Medicine", Jan. 1, 2016, XP055605749, vol. 951, pp. 123-135.
Xuan Zhou et al: "Differentiation of nonbeating embryonic stem cells into beating cardiomyocytes is dependent on downregulation of PKCbeta; and zeta in concert with upregulation of PKCepsilon", Development Biology, vol. 255, No. 2, Mar. 1, 2003, pp. 407-422, XP055240271.

(Continued)

*Primary Examiner* — Anoop K Singh
*Assistant Examiner* — David A Montanari
(74) *Attorney, Agent, or Firm* — K&L Gates LLP

(57) ABSTRACT

The disclosure provides a method of freezing an aggregate of pluripotent stem cell-derived cardiomyocytes, comprising:
(i) immersing an aggregate of pluripotent stem cell-derived cardiomyocytes in a cryoprotective solution; and
(ii) freezing the aggregate immersed in the cryoprotective solution.

The disclosure also provides a frozen aggregate of pluripotent stem cell-derived cardiomyocytes frozen by the method.

8 Claims, 10 Drawing Sheets

(56) References Cited

OTHER PUBLICATIONS

Extended European Search Report dated Jul. 26, 2019 issued in corresponding EP patent application No. 17766857.1.
Okawara Hirotatsu, et al., Examining the Long-term Preservations of iPS Stem Cell-Derived Myocardial Cel Sheets using Vitrification Cryopreservation, Feb. 1, 2016, vol. 15, p. 257, #O-39-5.
Kim YY, et al., Cryopreservation of human embryonic stem cells derived-cardiomyocytes induced by BMP2 in serum-free condition., Peprod Sci. Mar. 2011;18(3):252-60. doi:10.1177/1933719110385130. Epub Jan. 25, 2011.
Zhu W. Z. et al., Methods for assessing the electromechanical integration of human pluripotent stem cell-derived cardiomyocyte grafts. Methods in Molecular Biology, 2014, vol. 1181, pp. 229-247.
Burridge P.W. et al., Chemically defined culture and cardiomyocyte differentiation of human pluripotent stem cells. Current Protocols in Human Genetics, 2015, vol. Supp.87, Unit 21.3, pp. 1-15 DOI:10.1002/0471142905.hg2103s87.
Chen V.C. et al., Development of a scalable suspension culture for cardiac differentiation from human pluripotent stem cells. Stem Cell Research, 2015, vol. 15, pp. 365-375.
English translation of International Preliminary Report on Patentability dated Dec. 20, 2018 issued in the corresponding PCT application No. PCT/JP2017/010972.
Communication under Rule 71(3) EPC dated Jul. 27, 2022 in the corresponding European patent application No. 17766857.1; 8 pages.
Office Action dated May 25, 2021 issued in Japanese application No. 2018-506047 with English Machine Translation.
Macromolecules, 1968, vol. 17, No. 196, pp. 650-655.

\* cited by examiner

METHOD FOR FREEZING AGGREGATES OF PLURIPOTENT STEM CELL-DERIVED CARDIOMYOCYTES

CROSS-REFERENCE TO RELATED APPLICATIONS

The present application claims the benefit of International Application No. PCT/JP2017/010972, filed Mar. 17, 2017, which claims priority to Japanese Application No. 2016-055913, filed Mar. 18, 2016, the disclosures of which are incorporated herein by reference.

TECHNICAL FIELD

The present application claims priority to Japanese patent application No. 2016-055913, the whole of which is incorporated herein by reference.

The disclosure relates to methods for freezing an aggregate of pluripotent stem cell-derived cardiomyocytes.

BACKGROUND

Cardiomyocytes derived from pluripotent stem cells are expected to be put into practical use in applications such as cell transplantation, drug screening, and cardiotoxicity evaluation. Such practical applications would require mass production and supply of cardiomyocytes having the same functional property in one lot and efficient methods for cryopreservation of cardiomyocytes.

Current methods for freezing pluripotent stem cell-derived cardiomyocytes disperse sheet-like or colony-like aggregates of pluripotent stem cell-derived cardiomyocytes with proteolytic enzymes and freeze the dispersed cardiomyocytes in a single cell state. These methods result in unstable and low cell viability, and are difficult to reproduce uniform aggregates due to the damage by proteolytic enzymes or freezing. In addition, when cardiomyocytes are frozen in a single cell state, electrophysiological functional patterns before freezing (such as change in intracellular calcium wave or heart rate) are not reproduced after the cells are thawed. This would be because the information of three-dimensional structure such as the shape or intercellular binding of the original aggregate of cardiomyocytes is lost as cardiomyocytes are dispersed and frozen in a single cell state.

SUMMARY

An object of the disclosure is to provide a method of freezing an aggregate of pluripotent stem cell-derived cardiomyocytes and a frozen aggregate of pluripotent stem cell-derived cardiomyocytes.

In one embodiment, the disclosure provides a method of freezing an aggregate of pluripotent stem cell-derived cardiomyocytes, comprising:
  (i) immersing an aggregate of pluripotent stem cell-derived cardiomyocytes in a cryoprotective solution; and
  (ii) freezing the aggregate immersed in the cryoprotective solution.

In a further embodiment, the disclosure provides a method of preparing a frozen aggregate of pluripotent stem cell-derived cardiomyocytes, comprising:
  (i) immersing an aggregate of pluripotent stem cell-derived cardiomyocytes in a cryoprotective solution; and
  (ii) freezing the aggregate immersed in the cryoprotective solution.

In a further embodiment, the disclosure provides a frozen aggregate of pluripotent stem cell-derived cardiomyocytes that is frozen or prepared by the method.

In a further embodiment, the disclosure provides a frozen aggregate of pluripotent stem cell-derived cardiomyocytes for use in the evaluation of drug response or in the transplantation.

In a further embodiment, the disclosure provides a kit or a composition comprising a frozen aggregate of pluripotent stem cell-derived cardiomyocytes.

The method of freezing an aggregate of pluripotent stem cell-derived cardiomyocytes and the frozen aggregate of pluripotent stem cell-derived cardiomyocytes provided by the disclosure contribute to practical use of pluripotent stem cell-derived cardiomyocytes.

BRIEF DESCRIPTION OF DRAWINGS

FIG. 1-A shows the shape of an aggregate of cardiomyocytes on the third day after freeze-thaw of cells frozen by single cell freezing (one aggregate/well). FIG. 1-B shows the shape of an aggregate of cardiomyocytes on the second day after freeze-thaw of cells frozen by aggregate freezing.

DETAILED DESCRIPTION

Figure 1:
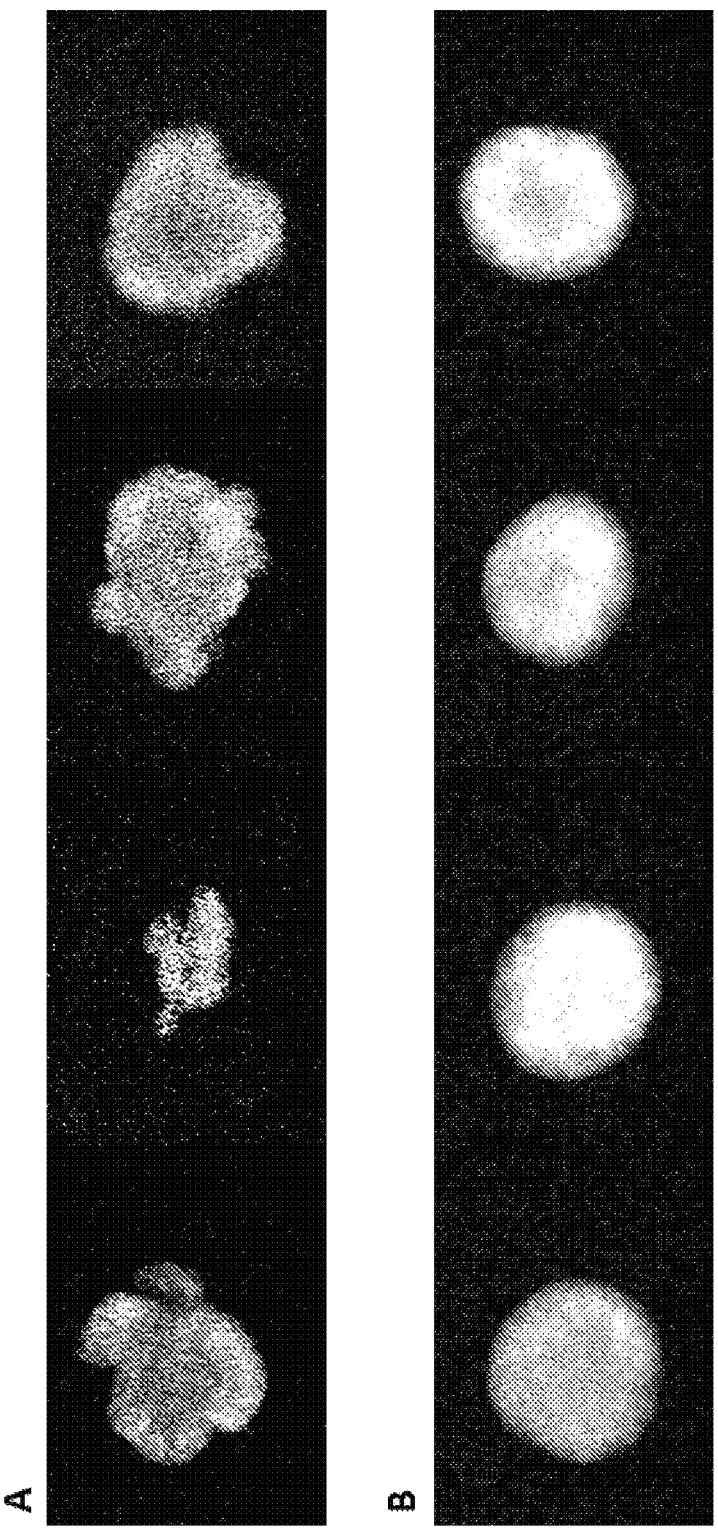
FIG. 1 shows the comparison of the shapes of aggregates of human iPS-derived cardiomyocytes from single cell freezing and aggregate freezing.

As used herein, a numerical value accompanied with the term "about" includes any value within the range of ±10% of that value. A numerical range defined by both ends covers all values between the both ends as well as the values at the both ends. A numerical range accompanied with the term "about" means that the values at both ends are accompanied with the term "about". For example, "about 20 to 30" means "20±10% to 30±10%".

The term "pluripotent stem cells" refers to cells having an ability to differentiate any type of cells constituting an adult body (pluripotency) and self-renewal capacity which is an ability to maintain the pluripotency during cell division. Examples of the "pluripotent stem cells" include embryonic stem cells (ES cells), embryonic germ cells (EG cells), and induced pluripotent stem cells (iPS cells). The "pluripotent stem cells" may be cells of any species with no limitation, and preferably mammalian cells, and more preferably rodent or primate cells. The present disclosure is suitable for monkey or human pluripotent stem cells, in particular monkey or human ES or iPS cells.

ES cells are pluripotent stem cells derived from early embryo and may be established from inner cell mass of a blastocyst or post-implantation epiblast in early embryo. Examples of ES cells include those described in the following references: human (Thomson J. A. et al., Science 282: 1145-1147 (1998), Biochem Biophys Res Commun. 345(3), 926-32 (2006); primates such as rhesus macaque and marmoset (Thomson J. A. et al., Proc. Natl. Acad. Sci. USA 92: 7844-7848 (1995); Thomson J. A. et al., Biol. Reprod. 55: 254-259 (1996)); rabbit (National Publication of International Patent Application No. 2000-508919); hamster (Doetshman T. et al., Dev. Biol. 127: 224-227 (1988)), hog (Evans M. J. et al., Theriogenology 33: 125128 (1990); Piedrahita J. A. et al., Theriogenology 34: 879-891 (1990); Notarianni E. et al., J. Reprod. Fert. 40: 51-56 (1990); Talbot N. C. et al., Cell. Dev. Biol. 29A: 546-554 (1993)), sheep (Notarianni E. et al., J. Reprod. Fert. Suppl. 43: 255-260 (1991)), cow (Evans M. J. et al., Theriogenology 33: 125-128 (1990); Saito S. et al., Roux. Arch. Dev. Biol. 201: 134-141 (1992)), and mink (Sukoyan M. A. et al., Mol. Reorod. Dev. 33: 418-431 (1993)). For example, ES cells such as CMK6.4, KhES-1, KhES-3, KhES-4, KhES-5, H1, and H9 may be used.

EG cells are pluripotent stem cells derived from primordial germ cells, and examples of EG cells include human EG cells (Shamblott, et al., Proc. Natl. Acad. Sci USA 95: 13726-13731 (1998)).

The term "iPS cells" refers to pluripotent stem cells induced from cells other than pluripotent stem cells such as somatic cells and tissue stem cells. Methods for preparing iPS cells are described, for example, in the following references: WO2007/069666, WO2009/006930, WO2009/006997, WO2009/007852, WO2008/118820, Cell Stem Cell 3(5): 568-574 (2008), Cell Stem Cell 4(5): 381-384 (2009), Nature 454: 646-650 (2008), Cell 136(3):411-419 (2009), Nature Biotechnology 26: 1269-1275 (2008), Cell Stem Cell 3: 475-479 (2008), Nature Cell Biology 11: 197-203 (2009), Cell 133(2): 250-264 (2008), Cell 131(5): 861-72 (2007), Science 318 (5858): 1917-20 (2007). In addition, the "iPS cells" of the disclosure include cells prepared by any method that artificially-induces pluripotent stem cells. iPS cells such as IMR90-1, IMR90-4, 201B7, and 253G1 may be used.

Pluripotent stem cell-derived cardiomyocytes refers to cardiomyocytes induced from pluripotent stem cells and are not limited to cells induced by any specific method. For example, pluripotent stem cell-derived cardiomyocytes may be induced by the method using BMP4 and activin A (Nat Biotechnol. 2007 September; 25(9):1015-24. Epub 2007 Aug. 26.); the method using agents such as activin A, FGF2, VEGFA, and Dkk1 (Cell Stem Cell. 2012 Jan. 6; 10(1):16-28. doi: 10.1016/j.stem.2011.12.013.); and the method using recombinant albumin and CHIR99021 and a WNT inhibitor (Nat Methods. 2014 August; 11(8):855-60. doi: 10.1038/nmeth.2999. Epub 2014 Jun. 15.). Cardiomyocytes such as iCell® Cardiomyocytes (Cellular Dynamics International, Inc.) or Cellartis® Cardiomyocytes (from P11012)/(from ChiPSA22) (Takara Bio Inc.) and cardiomyocytes induced in a similar way to those cardiomyocytes may also be used.

In a preferred embodiment, pluripotent stem cell-derived cardiomyocytes are cells induced by the method described in WO2015/182765. Specifically, pluripotent stem cell-derived cardiomyocytes may be obtained by the method comprising:
(1) culturing pluripotent stem cells in a medium containing a WNT signaling activator and a PKC activator; and
(2) culturing the cells obtained by the step (1) in a medium containing a WNT signaling inhibitor, a Src inhibitor, and an EGFR inhibitor.

The freezing method of the disclosure may further comprises obtaining pluripotent stem cell-derived cardiomyocytes prior to the step (i) by the method comprising:
(1) culturing pluripotent stem cells in a medium containing a WNT signaling activator and a PKC activator; and
(2) culturing the cells obtained by the step (1) in a medium containing a WNT signaling inhibitor, a Src inhibitor, and an EGFR inhibitor.

Pluripotent stem cell-derived cardiomyocytes may be cells induced by any one of the methods recited in this paragraph. Also, the freezing method of the disclosure may comprise obtaining pluripotent stem cell-derived cardiomyocytes by any one of the methods recited in this paragraph.

1. A method for inducing cardiac differentiation of pluripotent stem cells, which comprises the steps of:
   (1) culturing pluripotent stem cells in a medium containing a WNT signaling activator and a PKC activator; and
   (2) culturing the cells obtained by the step (1) in a medium containing a WNT signaling inhibitor, a Src inhibitor, and an EGFR inhibitor.
2. The method of item 1, wherein the WNT signaling inhibitor is a compound of Formula (I):

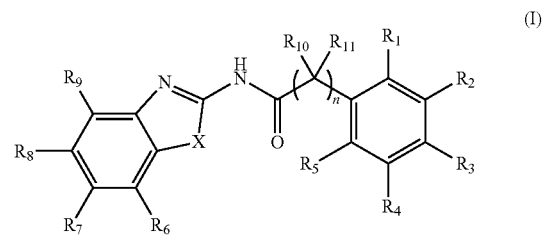

wherein
   $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—;
   $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—;

$R_{10}$ to $R_{11}$ are each independently a hydrogen atom; or a linear or branched alkyl group having 1 to 5 carbon atoms;

X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms; and n is an integer of 0 to 6;

or a salt thereof.

3. The method of item 2, wherein $R_4$, $R_5$, $R_6$, $R_9$, $R_{10}$, and $R_{11}$ are a hydrogen atom;

$R_2$ and $R_3$ are each independently a methoxy group, an ethoxy group or a propoxy group;

$R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom;

$R_8$ is a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom;

or $R_7$ and $R_8$ join together to form —O—$CH_2$—O— or —O—$(CH_2)_2$—O—;

X is a sulfur atom, and n is an integer of 0 to 4.

4. The method of item 2, wherein $R_1$, $R_4$, $R_5$, $R_6$, $R_8$, $R_9$, $R_{10}$, and $R_{11}$ are a hydrogen atom;

$R_2$ and $R_3$ are each independently a methoxy group, an ethoxy group or a propoxy group;

$R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom;

X is a sulfur atom, and n is an integer of 0 to 4.

5. The method of item 4, wherein $R_7$ is a halogen atom.

6. The method of any one of items 3-5, wherein n is an integer of 1 to 4.

7. The method of item 1, wherein the WNT signaling inhibitor is a compound selected from the group consisting of:

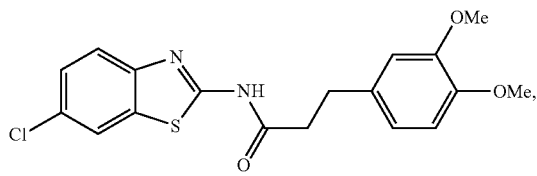
KY02111

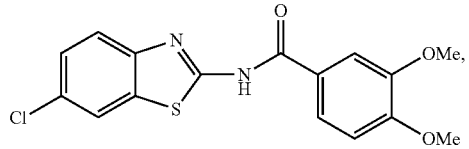
KY01041

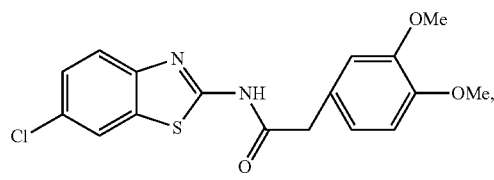
T61164

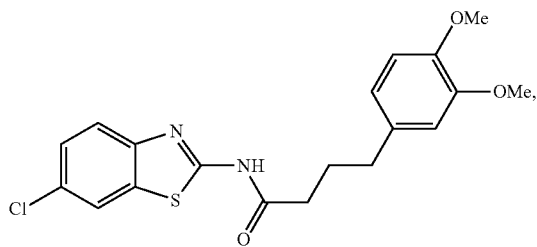
KY02114

KY01045
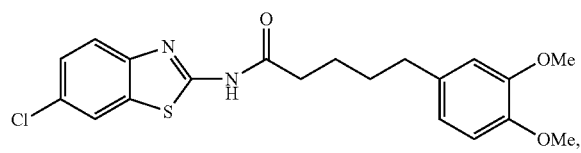
KY01040
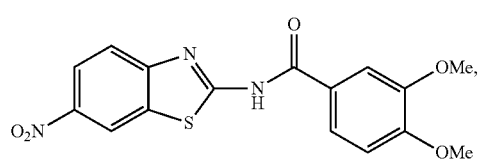
KY02109
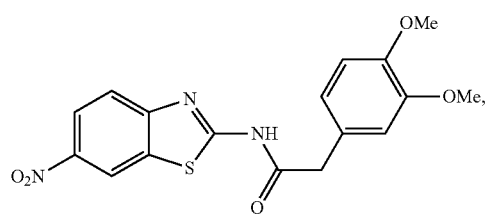
KY01042
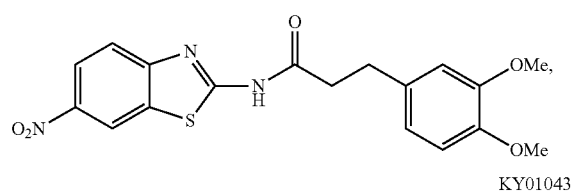
KY01043
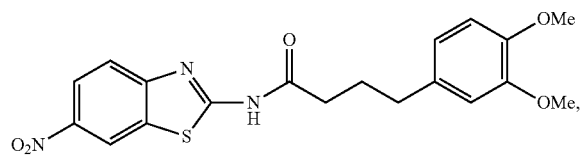
KY01046
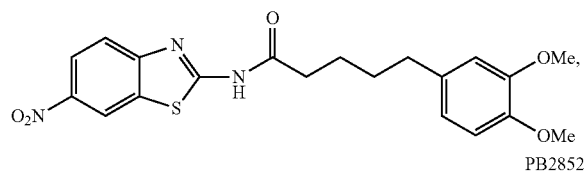
PB2852
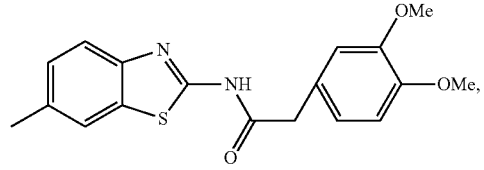
N11474
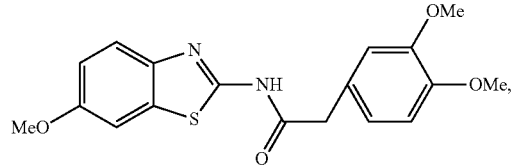
PB2572
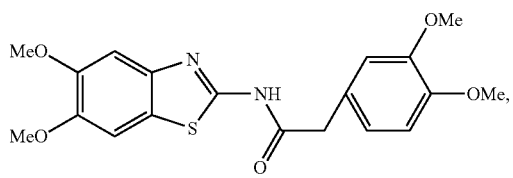
PB2570
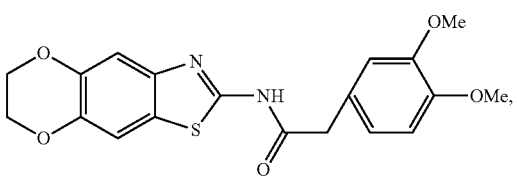
KY02104
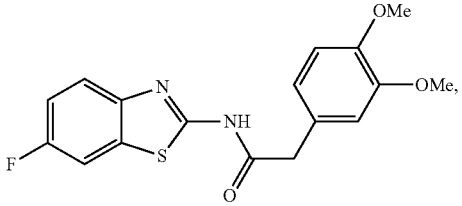
SO087
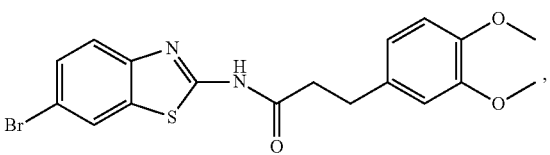
SO102
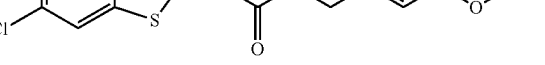
SO096
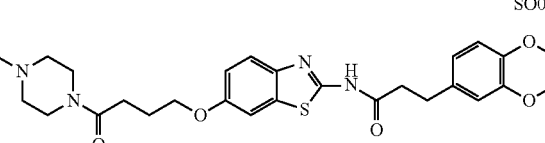
SO094
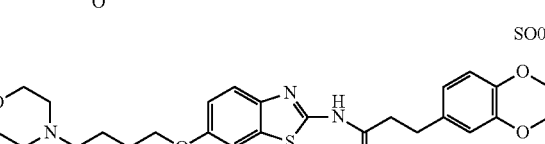
SO3031 (KY01-I)
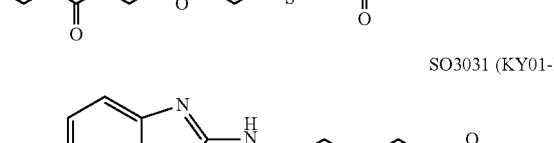
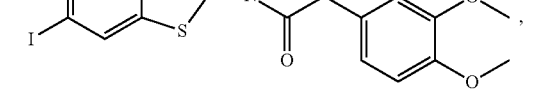

-continued

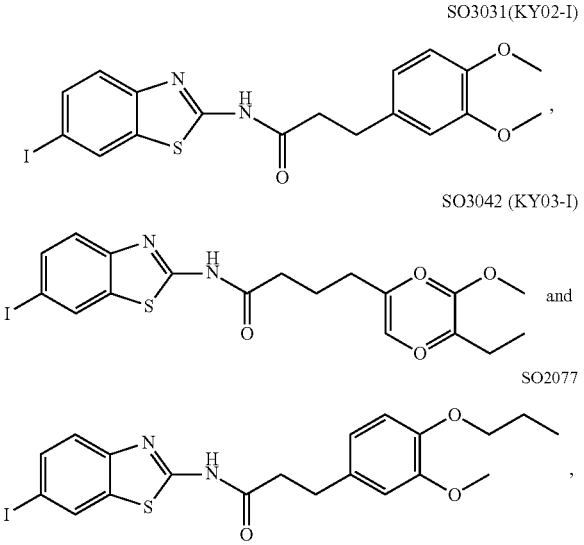

or a salt thereof.

8. The method of item 7, wherein the WNT signaling inhibitor is KY02111, SO3031 (KY01-I), SO2031 (KY02-I) or SO3042 (KY03-I).
9. The method of item 8, wherein the WNT signaling inhibitor is SO3042 (KY03-I).
10. The method of any one of items 1-9, wherein the medium of step (2) comprises two or more WNT signaling inhibitors, and wherein one of the two or more WNT signaling inhibitors is the compound of Formula (I) or a salt thereof as recited in any one of items 2-9, and one or more of the two or more WNT signaling inhibitors are selected from the group consisting of IWP2, XAV939, and IWR1.
11. The method of item 10, wherein the two or more WNT signaling inhibitors are the compound of Formula (I) or a salt thereof as recited in any one of items 2-9 and XAV939.
12. The method of any one of items 1-11, wherein the WNT signaling activator is BIO or CHIR99021.
13. The method of item 12, wherein the WNT signaling activator is CHIR99021.
14. The method of any one of items 1-13, wherein the PKC activator is PMA or prostratin.
15. The method of any one of items 1-14, wherein the PKC activator is PMA.
16. The method of any one of items 1-15, wherein the Src inhibitor is A419259 or SU6656.
17. The method of any one of items 1-16, wherein the Src inhibitor is A419259.
18. The method of any one of items 1-17, wherein the EGFR inhibitor is AG1478 or gefitinib.
19. The method of any one of items 1-18, wherein the EGFR inhibitor is AG1478.
20. The method of any one of items 1-19, wherein
the WNT signaling activator is CHIR99021,
the PKC activator is PMA,
the WNT signaling inhibitor comprises a compound selected from KY02111, SO3031 (KY01-I), SO2031 (KY02-I), and SO3042 (KY03-I), and XAV939,
the Src inhibitor is A419259, and
the EGFR inhibitor is AG1478.
21. The method of item 20, wherein the WNT signaling inhibitor comprises SO3042 (KY03-I) and XAV939.
22. The method of any one of items 1-21, wherein the medium of the step (1) and the medium of the step (2) do not contain any protein or peptide component.
23. The method of any one of items 1-22; wherein the culturing of the steps (1) and (2) is in suspension culture.
24. The method of any one of items 1-23, wherein the culturing of the step (1) is for 1 to 3 days and the culturing of the step (2) is for 2 to 13 days.

The "WNT signaling activator" refers to a substance that activates the WNT signaling pathway. Examples of WNT signaling activators include GSK3β inhibitors such as BIO, CHIR99021, and TWS119. In one embodiment, the WNT signaling activator is CHIR99021 or BIO, and preferably CHIR99021. In the method described in WO2015/182765, two or more WNT signaling activators may be used in combination. For example, both of CHIR99021 and BIO may be used.

The "WNT signaling inhibitor" refers to a substance that inhibits the WNT signaling pathway. Examples of WNT signaling inhibitors include the compound of formula (I) or a salt thereof as described herein, and compounds such as IWP2, IWP4, XAV939, and IWR1. In the present disclosure, two or more WNT signaling inhibitors may be used in combination. In one embodiment, one of the two or more WNT signaling inhibitors is the compound of formula (I) or a salt thereof, and the other is one or more compounds selected from IWP2, XAV939, and IWR1, and preferably XAV939. Each of the two or more WNT signaling inhibitors may be the compound of formula (I) or a salt thereof.

A linear or branched alkoxy group having 1 to 5 carbon atoms includes a methoxy group, an ethoxy group, a propoxy group, an isopropoxy group, a butoxy group, an isobutoxy group, a sec-butoxy group, a tert-butoxy group and a pentyloxy group.

A linear or branched alkyl group having 1 to 5 carbon atoms includes a methyl group, an ethyl group, a propyl group, an isopropyl group, a butyl group, an isobutyl group, a sec-butyl group, a tert-butyl group and a pentyl group.

A linear or branched acyl group having 1 to 5 carbon atoms includes a formyl group, an acetyl group, a propionyl group, a butyryl group, an isobutyryl group, a valeryl group and an isovaleryl group.

A halogen atom includes Cl, Br, I or F.

In a preferred embodiment, $R_1$ to $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—.

$R_2$ and $R_3$ are each preferably a linear or a branched alkoxy group having 1 to 5 carbon atoms or join together to form —O—$CH_2$—O— or —O—$(CH_2)_2$—O—. More preferably, $R_2$ and $R_3$ are each independently a methoxy group, an ethoxy group or a propoxy group, and further preferably a methoxy group.

$R_1$, $R_4$ and $R_5$ are each preferably a hydrogen atom.

In one embodiment, $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—CH$_2$—O— or —O—(CH$_2$)$_2$—O—.

$R_6$ and $R_9$ are preferably each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, more preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—CH$_2$—O— or —O—(CH$_2$)$_2$—O—.

In one embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom, and examples of such A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl groups which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

$R_{10}$ and $R_{11}$ are each preferably a hydrogen atom.

In one embodiment, n is an integer of 0 to 4, 1 to 4, or 1 to 3, or n is 2 or 3.

In one embodiment, X is an oxygen atom; a sulfur atom; or a group —NR$_{15}$, wherein R$_{15}$ is a hydrogen atom, a linear or branched alkyl group having 1 to 5 carbon atoms, a linear or branched acyl group having 1 to 5 carbon atoms. X is preferably a sulfur atom.

In one embodiment, the compound of formula (I) is the one:
wherein
$R_1$, $R_4$, $R_5$, $R_6$, $R_8$, $R_9$, $R_{10}$ and $R_{11}$ are each a hydrogen atom,
R7 is a halogen atom,
$R_2$ and $R_3$ are each independently a methoxy group, an ethoxy group or a propoxy group, X is a sulfur atom,
n is an integer of 0 to 4, preferably 1 to 4.

In one embodiment, the compound of formula (I) is the one:
wherein
$R_1$, $R_4$, $R_5$, $R_6$, $R_8$, $R_9$, $R_{10}$ and $R_{11}$ are each a hydrogen atom,
R7 is a halogen atom,
$R_2$ and $R_3$ are each a methoxy group,
X is a sulfur atom,
n is an integer of 0 to 4, preferably 1 to 4.

The compound of formula (I) is preferably KY02111, SO3031 (KY01-I), SO2031 (KY02-I), or SO3042 (KY03-I), more preferably KY02111 or SO3042 (KY03-I), even more preferably SO3042 (KY03-I).

The compound of Formula (I) may be synthesized by a known method (J. Med. Chem., 1965, 8 (5), pp 734-735) or in accordance with the methods described in WO2012/026491. Alternatively, they are available, for example, from UkrOrgSynthesis Ltd. (PB2852, PB2572, and PB2570) and ENAMINE (T61164).

The "PKC activator" refers to a substance that activates the signaling pathway of protein kinase C (PKC) or downstream therefrom. Examples of PKC activators include Phorbol 12-myristate 13-acetate (PMA), prostratin, Bryostatin 1, Bryostatin 2, FR236924, (−)-Indolactam V, PEP005, Phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA and Lipoxin A4. In one embodiment, the PKC activator is a phorbol ester-type PKC activator such as PMA, prostratin, PEP005, Phorbol 12,13-dibutyrate, Resiniferatoxin, Phorbol 12,13-Dihexanoate, Mezerein, or Ingenol 3-Angelate. Two or more PKC activators may be used in combination in the method described in WO2015/182765. In a preferred embodiment, the PKC activator is PMA or prostratin, more preferably PMA.

The "Src inhibitor" refers to a substance that inhibits the signaling pathway of Src tyrosine kinase or downstream therefrom. Examples of Src inhibitors include A419259, SU6656, PP1, 1-Naphthyl PP1, PP2, Indirubin-3'-(2,3-dihydroxypropyl)-oximether, TX-1123, Src Kinase Inhibitor I (CAS 179248-59-0), AZM475271, Bosutinib, Herbimycin A, KB SRC 4, MNS, PD166285 and TC-S7003. In one embodiment, the Src inhibitor is A419259, KB SRC 4, SU6656, or Indirubin-3'-(2,3-dihydroxypropyl)-oximether. Two or more Src inhibitors may be used in combination in the method described in WO2015/182765. In a preferred embodiment, the Src inhibitor is A419259 or SU6656, more preferably A419259.

The "EGF receptor inhibitor" (also described as EGFR inhibitor) refers to a substance that inhibits signaling from EGF receptor. Examples of EGF receptor inhibitors include AG1478, gefitinib, afatinib, ARRY334543, AST1306, AZD8931, BIBU1361, BIBX1382, BPDQ, BPIQ-I, BPIQ-II, canertinib, CL-387,785, CUDC101, dacomitinib, vandetanib, EGFR inhibitor (N-(4-((3,4-dichloro-6-CAS 733009-42-2), EGFR/ErbB-2 inhibitor (4-(4-benzyloxyanilino)-6,7-dimethoxyquinazoline, CAS 179248-61-4), erlotinib, GW583340, GW2974, HDS029, lapatinib, WHI-P154, OSI-420, PD153035, PD168393, PD174265, pelitinib, Compound 56, XL657, PP3, AG-490, AG555, tyrphostin B42, tyrphostin B44, AG556, AG494, AG825, RG-13022, DAPH, EGFR Inhibitor (cyclopropanecarboxylic acid (3-(6-(3-trifluoromethyl-phenylamino)-pyrimidin-4-ylamino)-phenyl)-amide, CAS 879127-07-8), erbstatin analog (methyl 2,5-dihydroxycinnamate, CAS 63177-57-1), JNJ28871063, tyrphostin 47, lavendustin A, lavendustin C, lavendustin C methylate, LFM-A12, TAK165, TAK285, tyrphostin 51, tyrphostin AG183, tyrphostin AG528, tyrphostin AG99, tyrphostin RG14620, WZ3146, WZ4002, WZ8040, butein, and tyrphostin AG112. In one embodiment, the EGF receptor inhibitor is an EGF receptor inhibitor having quinazoline structure, such as AG1478, gefitinib, afatinib, ARRY334543, AST1306, AZD8931, BIBU1361, BIBX1382, BPDQ, BPIQ-I, BPIQ-II, canertinib, CL-387, 785, CUDC101, dacomitinib, vandetanib, EGFR inhibitor III (CAS 733009-42-2), EGFR/ErbB-2 inhibitor (CAS 179248-61-4), erlotinib, GW583340, GW2974, HDS029, lapatinib, WHI-P154, OSI-420, PD153035, PD168393, PD174265, pelitinib, Compound 56, or XL657. In an preferred embodiment, the EGF receptor inhibitor is AG1478 or gefitinib, more preferably AG1478. EGF receptor inhibitors may be obtained, for example, from Santa Cruz Biotech.

The method described in WO2015/182765 is carried out in vitro. The method uses any conventional cardiac differentiation medium for pluripotent stem cells, not a medium having a specific composition. The medium preferably does not contain protein or peptide components, although the medium may contain such components. The medium described in WO2015/182765 contains, for example, IMDM medium and/or DMEM medium, MEM non-essential amino acid solution, and L-glutamine. In one embodiment, the medium contains IMDM medium and DMEM medium (preferably IMDM:DMEM=1:1), MEM non-essential amino acid solution, and L-Glutamine. The medium may contain L-carnitine, ascorbic acid, and/or creatine in addition to IMDM medium and/or DMEM medium, MEM non-essential amino acid solution, and L-glutamine. In a preferred embodiment, the medium contains IMDM medium and DMEM medium (preferably IMDM:DMEM=1:1), MEM non-essential amino acid solution, L-glutamine, L-carnitine, ascorbic acid, and creatine. The medium also may contain antibiotics, such as penicillin-streptomycin as required. Examples of the medium include IMDM and DMEM-based medium used in Examples (containing 242 ml of IMDM, 242 ml of DMDM, 5 ml of MEM non-essential amino acid solution (×100), 5 ml of penicillin-streptomycin (×100), 5 ml of 0.2 M L-glutamine, 100 µl of 1 M L-carnitine, 50 mg of ascorbic acid and 1 ml of 0.5 M creatine).

The method may use other types of medium, such as a cardiac differentiation medium based on IMDM medium known in the art (for example, a medium containing 200 ml of IMDM medium, 50 ml of bovine fetal serum, 2.5 ml of MEM non-essential amino acid solution (×100), 2.5 ml of 200 mM L-glutamine, 2 µl of 2-mercaptoethanol, 255 µl of 5N NaOH), a cardiac differentiation medium based on DMEM medium known in the art (for example, a medium containing 200 ml of DMEM/F12 medium, 50 ml of bovine fetal serum, 2.5 ml of MEM non-essential amino acid solution (×100), 2.5 ml of 200 mM L-glutamine, and 2-mercaptoethanol), or StemPro®-34SFM (GIBCO)+BMP4 (10 ng/ml).

Pluripotent stem cell-derived cardiomyocytes may be induced by any conventional culture method suitable for cardiac differentiation of pluripotent stem cells. Examples of culture methods include adhesion culture and suspension culture. In a preferred embodiment, pluripotent stem cell-derived cardiomyocytes are induced in suspension culture. The cell number of pluripotent stem cells on the start of culture may be appropriately determined by factors such as culture methods, culture vessels and types of cells, and the cells may be seeded at about 1×105 cells/ml to 10×105 cells/ml. The medium may be replaced once in one to three days, for example once in two days.

The period of each of the steps (1) and (2), and the period from the end of the step (1) to the start of the step (2) may be appropriately determined depending on factors such as types of cells. The step (2) may start just after the end of the step (1), or after a certain period from the end of the step (1). For example, after the end of the step (1), the cell may be cultured in a medium that does not contain a WNT signaling activator, a PKC activator, a WNT signaling inhibitor, a Src inhibitor nor an EGF receptor inhibitor for one or two days, preferably for one day, and then the medium may be replaced with a medium containing a WNT signaling inhibitor, a Src inhibitor and an EGF receptor inhibitor to start the step (2).

For example, the culturing of the step (1) may be for 1 to 3 days, and the step (2) may start just after the end of the step (1), or after 1 or 2 days from the end of the step (1). The culturing of the step (2) may be for 2 to 13 days, preferably for 3 to 10 days, more preferably for 4 to 10 days, even more for 4 to 8 days. For example, when the first day of the step (1) is Day 0, the step (1) may be from Day 0 to Day 1, Day 0 to Day 2 or Day 0 to Day 3, and the step (2) may be from Day 2 to Day 10 (for 8 days), Day 2 to Day 9 (for 7 days), Day 2 to Day 8 (for 6 days), Day 2 to Day 7 (for 5 days), Day 2 to Day 6 (for 4 days), Day 3 to Day 10 (for 7 days), Day 3 to Day 9 (for 6 days), Day 3 to Day 8 (for 5 days), Day 3 to Day 7 (for 4 days), Day 4 to Day 10 (for 6 days), Day 4 to Day 9 (for 5 days) or Day 4 to Day 8 (for 4 days) just after the end of the step (1), or after 1 or 2 days from the end of the step (1).

Since the step (1) corresponds to the early phase of cardiac differentiation at which pluripotent stem cells differentiate into mesoderm, the period of the step (1) may be determined based on the expression of a mesoderm-related gene. Examples of mesoderm-related genes include T, MIXL1, and NODAL. The step (2) corresponds to the late phase of cardiac differentiation at which the mesoderm differentiate into cardiomyocytes, and the period may be determined by detecting differentiation into cardiomyocytes. The differentiation into cardiomyocytes may be detected from, for example, the number of beating cardiac colonies, expression of a cardiac marker, expression of an ion channel, or a response to an electrophysiological stimulus. Examples of cardiac markers include α-MHC, β-MHC, cTnT, α-actinin, and NKX2.5. Also, examples of ion channels include HCN4, Nav1.5, Cav1.2, Cav3.2 HERG1b and KCNQ1.

The WNT signaling activator and WNT signaling inhibitor may be used at a concentration appropriately determined based on the cells and agents to be used. When the WNT signaling activator is BIO or CHIR99021, for example, the WNT signaling activator may be used at a final concentration of 100 nM to 100 µM, preferably 1 µM to 10 µM. When the WNT signaling inhibitor is IWP2, XAV939, or IWR1, the WNT signaling inhibitor may be used, for example, at a final concentration of 0.5 to 20 µM, preferably 0.5 to 10 µM, more preferably 1 to 10 µM. When the WNT signaling inhibitor is the compound of Formula (I) or a salt thereof, the WNT signaling inhibitor may be used, for example, at a final concentration of 0.1 to 20 µM, preferably 0.1 to 10 µM, more preferably 1 to 10 µM, depending on the compound or salt to be used.

The PKC activator may be used at a concentration appropriately determined based on the cells and agent to be used. When the PKC activator is PMA, for example, the PKC activator may be used at a final concentration of 0.01 µM to 10 µM, preferably 0.03 to 1 µM, more preferably 0.1 to 1 µM. When the PKC activator is prostratin, for example, the PKC activator may be used at a final concentration of 0.1 µM to 100 µM, preferably 1 to 10 µM.

The Src inhibitor may be used at a concentration appropriately determined based on the cells and agent to be used. When the Src inhibitor is A419259 or SU6656, for example, the Src inhibitor may be used at a final concentration of 0.1 µM to 10 µM, preferably 0.1 to 3 µM, more preferably 0.3 to 3 µM.

The EGF receptor inhibitor may be used at a concentration appropriately determined based on the cells and agent to be used. When the EGF receptor inhibitor is gefitinib or AG1478, for example, the EGF receptor inhibitor may be used at a final concentration of 100 nM to 100 µM, preferably 1 to 20 µM. When the EGF receptor inhibitor is PP3, for example, the EGF receptor inhibitor may be used at a final concentration of 1 µM to 1 mM, preferably 10 µM to 100 µM.

Preferably, after the step (2), the medium is replaced with a cardiac differentiation medium that does not contain a WNT signaling inhibitor, a Src inhibitor, and a EGF receptor inhibitor, and then the cardiomyocytes are cultured for several days, weeks, or months, preferably about 1 week to 3 months, more preferably from about 3 weeks to 3 months, before freezing.

Pluripotent stem cell-derived cardiomyocytes may be induced from pluripotent stem cells that express a calcium sensor protein such as a GFP-calmodulin-myosin light chain fragment-binding protein (also referred to as a GCaMP series protein herein) or a membrane potential sensor protein such as VSFP such that the change of intracellular $Ca^{2+}$ concentration is detectable. Thus, one embodiment, pluripotent stem cells or pluripotent stem cell-derived cardiomyocytes express a calcium sensor protein, preferably a GCaMP series protein. Examples of GCaMP series proteins include GCaMP, GCaMP2, GCaMP3, and GCaMP7. Cardiomyocytes expressing a calcium sensor protein that emits fluorescence by binding to $Ca^{2+}$ enables detection of the change of intracellular $Ca^{2+}$ concentration from the change of fluorescence intensity, and visualization myocardial beating by fluorescence. $Ca^{2+}$ is suitable for practical use, such as cardiotoxicity evaluation, as it directly triggers muscle contraction. Also, measurements using such cardiomyocytes do not require extracellular electrodes and thus may be carried out in suspension without being affected by the state of cell-electrode attachment, and may be carried out repeatedly using the same aggregate of cardiomyocytes for a long time by washing out the agent added to the aggregate.

Figure 2:
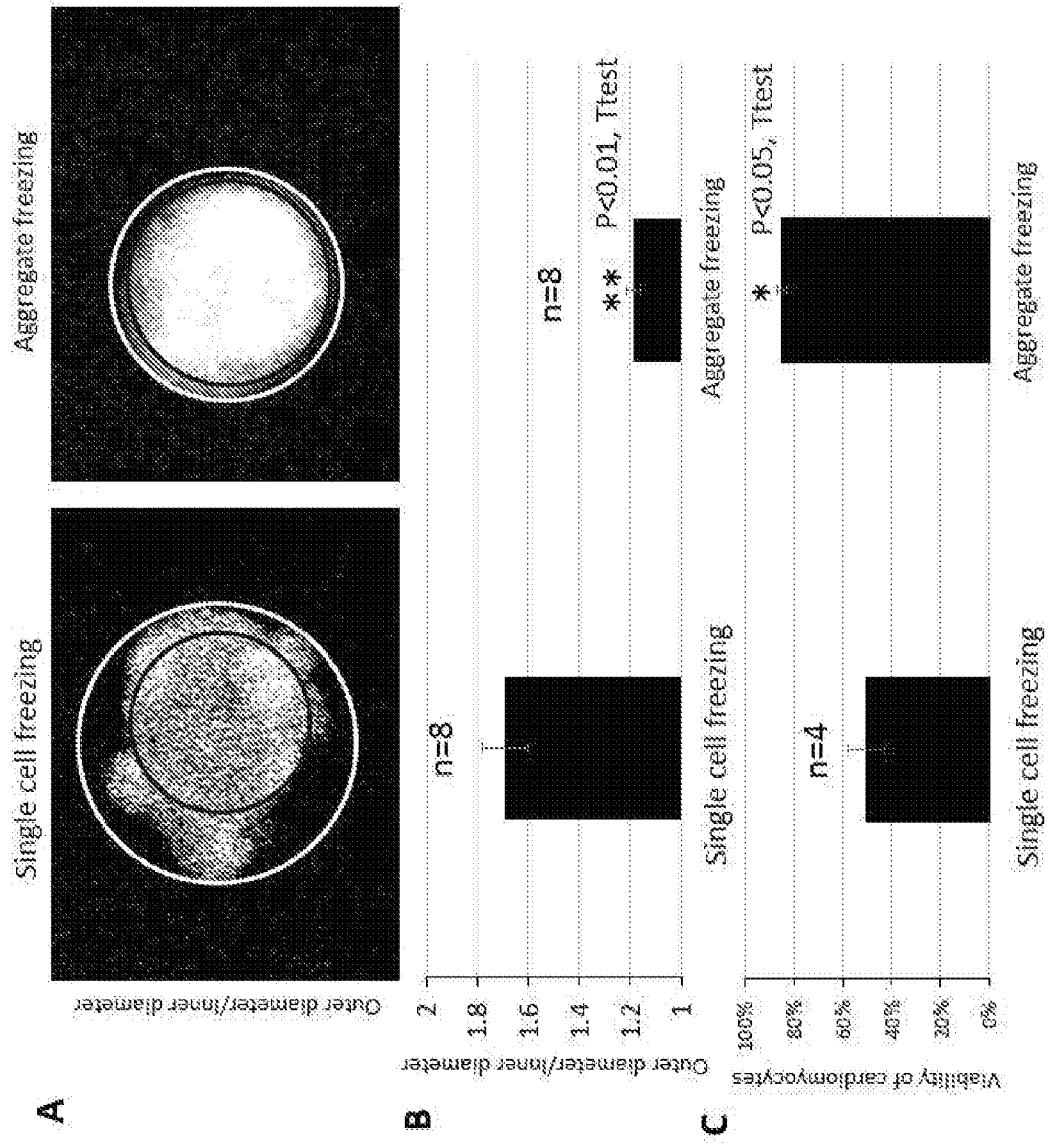
FIGS. 2A, 2B, and 2C show the analysis of the shape of an aggregate and the quantitative comparison of cell viability between single cell freezing and aggregate freezing.

An aggregate of pluripotent stem cell-derived cardiomyocytes to be frozen by the freezing method of the present disclosure may have a diameter of 50 to 5000 µm. Preferably, the aggregate has a diameter of 50 to 3000 µm, 50 to 2000 µm, 100 to 3000 µm or 100 to 2000 µm. In one embodiment, the aggregate has a diameter of 200 to 2000 µm, preferably 500 to 1000 µm. The diameter of an aggregate means the outer diameter of the aggregate as shown in FIG. 2.

The aggregate of pluripotent stem cell-derived cardiomyocytes may be obtained by dispersing an aggregate of cardiomyocytes induced by differentiation of pluripotent stem cells into single cells and re-forming an aggregate. Alternatively, the aggregate of cardiomyocytes induced by differentiation of pluripotent stem cells may be frozen directly (that is, without dispersion into single cells and re-formation of an aggregate).

Thus, the method of the disclosure may comprise prior to the step (i):
(a) dispersing an aggregate of cardiomyocytes induced by differentiation of pluripotent stem cells into single cells with a proteolytic enzyme; and
(b) seeding the cells obtained by the step (a) on a container and culturing to prepare an aggregate.

The dispersing an aggregate into single cells may use a solution containing a proteolytic enzyme such as trypsin/collagenase solution or TrypLE select. The cells obtained by dispersing an aggregate into single cells are seeded on a container at 0.3 to 30×10⁵ cells/cm² and cultured to prepare an aggregate of cardiomyocytes in the size as described herein. Examples of containers for culturing are the same as those for immersing an aggregate in a cryoprotective solution described hereinafter. Thus, the preparing an aggregate and the immersing the aggregate in a cryoprotective solution may be carried out in one container. As an example, when a 96-well plate is used, cells are preferably seeded at 0.1 to 10×10⁵ cells/well, preferably 0.5 to 2×10⁵ cells/well. The culture period in general may be appropriately determined within, but not limited to, 3 to 180 days. In one embodiment, the culture period is 14 to 30 days.

The immersing an aggregate of pluripotent stem cell-derived cardiomyocytes in a cryoprotective solution is carried out in a container such as a multi-well plate, dish, or tube. The container may be a commercially available container for freezing cells, and may be a container made of polyethylene, polypropylene, polystyrene, or glass. The multi-well plate may be a 6, 12, 24, 48, 96, or 384-well, flat, U-bottom, or V-bottom plate. For example, Sumilon Prime-Surface® 96-well V-bottom plate may be used.

The cryoprotective solution may be a commercially available cryoprotective solution such as, but not limited to, CELLBANKER 1 (Nippon Zenyaku Kogyo Co., Ltd.), STEM-CELLBANKER (Nippon Zenyaku Kogyo Co., Ltd.), or BAMBANKER (NIPPON Genetics Co, Ltd.). Also, one skilled in the art is capable of preparing a suitable cryoprotective solution. The cryoprotective solution may comprise a conventional cryoprotective agent. Preferably, the cryoprotective solution comprises DMSO or glycerol. For example, the cryoprotective solution may be serum comprising DMSO or glycerol. In some embodiments, the cryoprotective solution comprises about 5-20% DMSO or about 5-20% glycerol.

Preferably, the aggregate is immersed in a cryoprotective solution at 2 to 24° C., more preferably at 2 to 10° C., even more preferably at about 4° C. The period of immersion is, for example, 5 to 60 minutes, more preferably 10 to 40 minutes, even more preferably 10 to 30 minutes, even more preferably 20 to 30 minutes. The cryoprotective solution is added in an amount that sufficiently covers the cell aggregate. For example, when a 96-well plate is used, the amount of the cryoprotective solution may be 5 to 30 µl/well.

The aggregate is frozen after the immersion in the cryoprotective solution. The aggregate is frozen preferably at −60 to −150° C., more preferably at −60 to −100° C., even more preferably at −70 to −90° C., even more preferably at about −80° C. The container containing the aggregate may be put in a conventional freezing vessel such as BICELL biofreezing vessel and frozen in a freezer. When the temperature is lowered over time (for example, at 0.1 to 1° C./minute), for example by using a program freezer, the period of immersion in a cryoprotective solution may be less than 5 minutes. The amount of the cryoprotective solution is preferred to be small at the freezing, and thus excess cryoprotective solution is preferably removed to the extent that the cell aggregate is not exposed. For example, when a 96-well plate is used, excess cryoprotective solution is removed such that the cryoprotective solution remains at 5 to 20 μl/well. After the freezing at the temperature, the frozen aggregate may be stored at −140 to −150° C.

The frozen aggregate is thawed prior to use. For example, the frozen aggregate may be thawed by adding a culturing medium for cardiomyocytes to the container containing the frozen aggregate. The medium may be, but not limited to, an IMDM and/or DMEM-based medium for culturing cardiomyocytes. The medium for cardiac differentiation used in the method described in WO2015/182765 may also be used for thawing. For example, the medium may comprise IMDM medium and/or DMEM medium, MEM non-essential amino acid solution, and L-glutamine. In one embodiment, the medium comprises IMDM medium and DMEM medium (preferably IMDM:DMEM=1:1), MEM non-essential amino acid solution, and L-glutamine. In addition to IMDM medium and/or DMEM medium, MEM non-essential amino acid solution, and L-glutamine, the medium may comprise L-carnitine, ascorbic acid and/or creatine. In a preferred embodiment, the medium comprises IMDM medium and DMEM medium (preferably IMDM:DMEM=1:1), MEM non-essential amino acid solution, L-glutamine, L-carnitine, ascorbic acid, and creatine. Where necessary, the medium may comprise an antibiotic such as penicillin-streptomycin. A specific example of the medium is the IMDM and DMEM-based medium used in Examples (containing 242 ml of IMDM, 242 ml of DMDM, 5 ml of MEM non-essential amino acid solution (×100), 5 ml of penicillin-streptomycin (×100), 5 ml of 0.2 M L-glutamine, 100 μl of 1 M L-carnitine, 50 mg of ascorbic acid, and 1 ml of 0.5 M creatine).

The thawing medium preferably comprises serum (for example fetal bovine serum (FBS) or human serum), and further preferably comprises serum and a Rock inhibitor. Preferably, the thawing medium comprises 5-30% serum, preferably about 20% serum. More preferably, in addition to serum, the thawing medium comprises 1 to 10 μM Rock inhibitor, preferably about 3 μM Rock inhibitor. Examples of Rock inhibitors include Y27632, Fasudil, and Ripasudil.

It is desirable that the thawing is carried out as quick as possible. For example, the thawing medium warmed to about 37° C. is added to the container containing the frozen aggregate in an amount 5 times or more, preferably 10 times or more that of the cryoprotective solution in the container. After the supernatant is promptly discarded, the thawing medium is added to the container again for culturing. When the thawing medium comprises a Rock inhibitor, the whole medium is replaced with a medium containing no Rock inhibitor on the next day of thawing. From the next day of thawing, for example 1 to 7 days after thawing, the cells may be used in functional analysis.

Also provided is a method of freezing and thawing an aggregate of pluripotent stem cell-derived cardiomyocytes, comprising:
  (i) immersing an aggregate of pluripotent stem cell-derived cardiomyocytes in a cryoprotective solution;
  (ii) freezing the aggregate immersed in the cryoprotective solution; and
  (iii) thawing the frozen aggregate with a medium comprising serum and a Rock inhibitor.

The steps (i) and (ii) are carried out as described with regard to the freezing method of the disclosure. In one embodiment, the step (iii) comprises:
  adding a medium comprising serum and a Rock inhibitor and warmed to about 37° C. to a container containing the frozen aggregate, preferably in an amount 5 times or more, more preferably 10 times or more that of the cryoprotective solution in the container;
  promptly discarding the supernatant and adding again the medium to the container; and
  replacing the medium with a medium comprising serum but no Rock inhibitor on the next day.

The freezing method of the disclosure produces a frozen aggregate of pluripotent stem cell-derived cardiomyocytes. That is, also provided is a method of preparing a frozen aggregate of pluripotent stem cell-derived cardiomyocytes. In addition, also provided is a composition comprising a frozen aggregate of pluripotent stem cell-derived cardiomyocyte. In one embodiment, the composition of the disclosure comprises a frozen aggregate of pluripotent stem cell-derived cardiomyocytes and a cryoprotective solution.

For use in the evaluation of drug response such as cardiotoxicity evaluation or drug screening or in the transplantation, frozen cardiomyocytes should maintain electrophysiological properties (such as change in intracellular calcium wave and heart rate) or drug response before frozen after they are thawed. Also, it is desirable that frozen cardiomyocytes are easily thawed and the viability after thawed is high. The frozen aggregate of pluripotent stem cell-derived cardiomyocytes of the disclosure maintains sufficient electrophysiological properties and drug response to these applications after thawed, and may be used in the evaluation of drug response or in the transplantation. In addition, the frozen aggregate of pluripotent stem cell-derived cardiomyocytes of the disclosure may be thawed in a simple operation and show a high viability after thawed. In one embodiment of the frozen aggregate of pluripotent stem cell-derived cardiomyocytes of the disclosure, the cardiomyocytes show the cell viability of 70% or more, preferably 80% or more after the aggregate is thawed. The cell viability may be calculated from the number of living cells and the total cell number that may be obtained by counting the numbers of living cells and dead cells with a technique that distinguishes these cells such as trypan blue staining.

When cardiomyocytes express a calcium sensor protein such as GCaMP or a membrane potential sensor protein such as VSFP, the change in intracellular calcium concentration or membrane potential may be detected as a change in fluorescence intensity, and the beating of cardiomyocytes may be visualized by fluorescence. Cardiomyocytes that do not express any calcium sensor protein may be used with a calcium indicator such as Fluo-4, Fluo-8, or Fura-2, voltage-sensitive dye such as DiOC, or extracellular electrodes for the evaluation of drug response.

The frozen aggregate of pluripotent stem cell-derived cardiomyocytes of the disclosure may be provided as a kit for use in an application such as the evaluation of drug response or the transplantation. The kit may comprise a container suitable for its application (such as a microplate, dish or tube) and the container may comprise the frozen aggregate of pluripotent stem cell-derived cardiomyocytes. The kit may further comprise a thawing medium and/or a culturing medium and other necessary reagents.

In particular, pluripotent stem cell-derived cardiomyocytes induced by the method described in WO 2015/182765 and frozen by the freezing method of the disclosure may provide a frozen aggregate of pluripotent stem cell-derived cardiomyocytes or a kit comprising the same that is more suitable to the evaluation of drug response such as cardiotoxicity evaluation or drug screening.

In one embodiment of the composition or kit comprising a frozen aggregate of pluripotent stem cell-derived cardiomyocytes, 10% or more of pluripotent stem cell-derived cardiomyocytes in the composition or kit forms an aggregate(s) having a diameter of 50 to 5000 μm. Preferably, 10% or more of pluripotent stem cell-derived cardiomyocytes in the composition or kit forms an aggregate(s) having a diameter of 50 to 3000 μm, 50 to 2000 μm, 100 to 3000 μm, or 100 to 2000 μm. In one embodiment, 10% or more of pluripotent stem cell-derived cardiomyocytes in the composition or kit forms an aggregate(s) having a diameter of 200 to 2000 μm or 500 to 1000 μm. In a further embodiment, 20, 30, 40, 50, 60, 70, 80% 90%, or 95% or more of pluripotent stem cell-derived cardiomyocytes in the composition or kit may form an aggregate(s) having a predetermined diameter. In a preferred embodiment, 70, 80%, 90%, or 95% or more of pluripotent stem cell-derived cardiomyocytes in the composition or kit may form an aggregate(s) having a predetermined diameter.

The method described in WO 2015/182765 induces cardiomyocytes from pluripotent stem cells at low cost with high efficiency, and thus enables mass production of cardiomyocytes. The cardiomyocytes induced by the method express relatively high levels of channel genes (such as HERG and KCNQ1), have similar electrophysiological properties to those of relatively matured cardiomyocytes in patch clamp technique, and show prolongation of action potential (QT extension) by inhibitors for the channels such as E4031 and chromanol 293b. The freezing method of the disclosure enables freezing and storing induced cardiomyocytes while maintaining their viability and functionality. Thus, cardiomyocytes in one lot may be produced and stored in a large scale, and cells having secure electrophysiological properties may be supplied at any time. Thus, new systems for drug evaluation in place of animal testing or HERG channel test would be provided.

Examples of embodiments of the disclosure are provided hereinafter.

1. A method of freezing an aggregate of pluripotent stem cell-derived cardiomyocytes, comprising:
   (i) immersing an aggregate of pluripotent stem cell-derived cardiomyocytes in a cryoprotective solution; and
   (ii) freezing the aggregate immersed in the cryoprotective solution.
2. A method of preparing a frozen aggregate of pluripotent stem cell-derived cardiomyocytes, comprising:
   (i) immersing an aggregate of pluripotent stem cell-derived cardiomyocytes in a cryoprotective solution; and
   (ii) freezing the aggregate immersed in the cryoprotective solution.
3. The method of item 1 or 2, wherein the aggregate is immersed in the cryoprotective solution for 5 to 60 minutes.
4. The method of any one of items 1-3, wherein the aggregate is immersed in the cryoprotective solution for 10 to 30 minutes.
5. The method of any one of items 1-4, wherein the aggregate is immersed in the cryoprotective solution at 2 to 24° C.
6. The method of any one of items 1-5, wherein the aggregate is immersed in the cryoprotective solution at 2 to 10° C.
7. The method of any one of items 1-6, wherein the aggregate is frozen at −60 to −150° C.
8. The method of any one of items 1-7, wherein the aggregate is frozen at −70 to −90° C.
9. The method of any one of items 1-8, wherein the aggregate has a diameter of 50 to 5000 μm.
10. The method of any one of items 1-9, wherein the aggregate has a diameter of 50 to 2000 μm.
11. The method of any one of items 1-10, wherein the aggregate has a diameter of 100 to 2000 μm.
12. The method of any one of items 1-11, wherein the pluripotent stem cell-derived cardiomyocytes express GFP-calmodulin-myosin light chain fragment-binding protein.
13. The method of any one of items 1-12, wherein the pluripotent stem cell-derived cardiomyocytes are cells obtained by the method comprising:
   (1) culturing pluripotent stem cells in a medium containing a WNT signaling activator and a PKC activator; and
   (2) culturing the cells obtained by the step (1) in a medium containing a WNT signaling inhibitor, a Src inhibitor, and an EGFR inhibitor.
14. The method of any one of items 1-13, wherein the method further comprises obtaining pluripotent stem cell-derived cardiomyocytes prior to the step (i) by the method comprising:
   (1) culturing pluripotent stem cells in a medium containing a WNT signaling activator and a PKC activator; and
   (2) culturing the cells obtained by the step (1) in a medium containing a WNT signaling inhibitor, a Src inhibitor, and an EGFR inhibitor.
15. The method of any one of items 1-14, wherein the pluripotent stem cells are human or monkey pluripotent stem cells.
16. The method of any one of items 1-15, wherein the pluripotent stem cells are human iPS cells.
17. The method of any one of items 1-16, wherein the pluripotent stem cells express GFP-calmodulin-myosin light chain fragment-binding protein.
18. The method of any one of items 1-17, wherein the cryoprotective solution comprises DMSO or glycerol.
19. A frozen aggregate of pluripotent stem cell-derived cardiomyocytes that is frozen or prepared by the method of any one of items 1-18.
20. A frozen aggregate of pluripotent stem cell-derived cardiomyocytes for use in the evaluation of drug response or in the transplantation.
21. The frozen aggregate of pluripotent stem cell-derived cardiomyocytes of item 19 or 20, wherein the cardiomyocytes show the viability of 70% or more after the aggregate is thawed.
22. The frozen aggregate of pluripotent stem cell-derived cardiomyocytes of items 19-21, wherein the aggregate has a diameter of 50 to 5000 μm.
23. The frozen aggregate of pluripotent stem cell-derived cardiomyocytes of items 19-22, wherein the aggregate has a diameter of 50 to 2000 μm.
24. The frozen aggregate of pluripotent stem cell-derived cardiomyocytes of items 19-23, wherein the aggregate has a diameter of 100 to 2000 μm.
25. A frozen aggregate of pluripotent stem cell-derived cardiomyocytes that has a diameter of 50 to 5000 μm.
26. The frozen aggregate of pluripotent stem cell-derived cardiomyocytes of item 25, wherein the aggregate has a diameter of 50 to 2000 m.
27. The frozen aggregate of pluripotent stem cell-derived cardiomyocytes of item 25 or 26, wherein the aggregate has a diameter of 100 to 2000 μm.
28. A kit comprising the frozen aggregate of pluripotent stem cell-derived cardiomyocytes of any one of items 19-27.

29. The kit of item 28, wherein the kit further comprises a multi-well plate, a dish, or a tube.
30. The kit of item 28 or 29, wherein the kit further comprises a thawing medium and/or a culturing medium.
31. The kit of any one of items 28-30, wherein the kit is for use in the evaluation of drug response or in the transplantation.
32. A composition comprising a frozen aggregate of pluripotent stem cell-derived cardiomyocytes that has a diameter of 50 to 5000 μm.
33. The composition of item 32, wherein the aggregate has a diameter of 50 to 2000 μm.
34. The composition of item 32 or 33, wherein the aggregate has a diameter of 100 to 2000 μm.
35. The composition of any one of items 32-34, wherein the composition is for use in the evaluation of drug response or in the transplantation.
36. Use of the frozen aggregate of pluripotent stem cell-derived cardiomyocytes of any one of items 19-27, the kit of any one of items 28-31, or the composition of any one of items 32-34, in the evaluation of drug response or in the transplantation.

The invention is further described with reference to the following examples, but not limited by the examples in any sense.

EXAMPLES

1. Comparison of Shapes of Aggregates of Human iPS-Derived Cardiomyocytes from Single Cell Freezing and Aggregate Freezing An aggregate of cardiomyocytes was prepared from human iPS cells (253G1 strain) according to the method described in WO2015/182765. Specifically, in the early phase of cardiac differentiation (day 0-2), floating colonies of human iPS cells (253G1 strain) (prepared according to Minami, I. et al., Cell reports 2, 1448-1460 (2012) and WO 2013/111875) were cultured in the medium of Table 1 (referred to as protein-free cardiac differentiation (PFCD) medium hereinafter) supplemented with a GSK3β inhibitor (2 μM CHIR99021) and a PKC activator (0.3 μM PMA) in suspension culture. Next, the colonies were cultured in PFCD medium without the GSK3β inhibitor and the PKC activator for one day (day 2-3), and in the late phase of cardiac differentiation (day 3-7), cultured for four days in PFCD medium supplemented with WNT signaling inhibitors (3 μM KY03-I and 1 μM XAV939) and an EGFR inhibitor (10 μM AG1478), and a Src inhibitor (0.3 μM A419259) in suspension culture (on a low adhesion dish (Wako 641-07391 or Corning YO-01835-24)). The colonies were then cultured in PFCD medium without the WNT signaling inhibitors, EGFR inhibitor and Src inhibitor for 21-30 days and used in the following experiments.

TABLE 1

| Formulation | Cat. No. | Amount |
| --- | --- | --- |
| IMDM | Sigma 13390 | 242 ml |
| DMEM | Sigma D5796 | 242 ml |
| MEM non-essential amino acid | Sigma M7145 | 5 ml |
| Penicillin-Streptomycin | GIBCO 15140 | 5 ml |
| 0.2M L-glutamine | Sigma G7513 | 5 ml |
| 1M L-carnitine | Sigma C0283 | 100 μl |

TABLE 1-continued

| Formulation | Cat. No. | Amount |
| --- | --- | --- |
| Ascorbic acid | Sigma A5960 | 50 mg |
| 0.5M creatine | Sigma C0780 | 1 ml |
| Total | | 500 ml |

For single cell freezing, the colonies of cardiomyocytes thus obtained were dispersed into single cells with trypsin/collagenase solution and the medium was immediately replaced with a cryoprotective solution (CELLBANKER 1, Nippon Zenyaku Kogyo Co., Ltd.) and frozen at −80° C. in CryoTube (Nunc). For aggregate freezing, the aggregates of cardiomyocytes thus obtained were dispersed into single cells with trypsin/collagenase solution, and seeded on Sumilon PrimeSurface 96-well V-bottom plates at $1×10^3$ cells/well and cultured for seven days to form an aggregate (700 to 1000 μm in diameter). Then, the medium was replaced with the cryoprotective solution (CELLBANKER 1). After the plates were left to stand for 20 minutes at 4° C., excess cryoprotective solution was discarded such that the amount of the cryoprotective solution was 5 to 20 μl/well, and the plates were frozen at −80° C.

To prepare a thawing medium, PFCD medium supplemented with 20% fetal bovine serum (FBS) and 3 μM Rock inhibitor (Y-27632) was warmed to 37° C. To thaw the sample of single cell freezing, the thawing medium (10 ml) was quickly added to the sample. After the supernatant was discarded, the cells were suspended with the thawing medium and seeded on Sumilon PrimeSurface 96-well V-bottom plates at $1×10^5$ cells/well. On the following day, the whole medium was replaced with PFCD medium supplemented with 10% FBS (containing no Rock inhibitor). The cells were cultured for three days to form an aggregate to be analyzed (FIG. 1-A). To thaw the sample of aggregate freezing, the thawing medium (200 μl/well) was quickly added to each well. After the supernatant was discarded, the thawing medium was added to each well for culturing. On the following day, the whole medium was replaced with PFCD medium supplemented with 10% FBS (containing no Rock inhibitor). The aggregate was cultured for two days and then analyzed (FIG. 1-B).

The aggregates formed from cells after single cell freezing significantly varied in size and shape among wells (FIG. 1-A). This was believed to be due to the variation of cell viability or the instability of cell-cell adhesion. On the other hand, when cells were frozen after aggregates were formed, the freeze-thawed aggregates were uniform and had high viability while maintaining their size and shape (FIG. 1-B).

2. Analysis of Shapes of Aggregates from Single Cell Freezing and Aggregate Freezing and Quantitative Comparison of Cell Viability Between Single Cell Freezing and Aggregate Freezing The outer and inner diameters of the aggregates of FIG. 1-A and FIG. 1-B were measured (FIG. 2-A) and the ratio of the outer and inner diameters was calculated (FIG. 2-B). When the cells were frozen as an aggregate, the freeze-thawed aggregate showed small difference between the outer and inner diameters and was almost spherical in shape. The cell number was also counted with cell counter before and after freeze-thaw in single cell freezing and aggregate freezing to compare cell viability (FIG. 2-C). While the cell viability in single cell freezing was around 50%, the cell viability in aggregate freezing was stably high and around 85%.

3. Preparation of GCaMP Positive iPS Cell-Derived Cardiomyocytes

A gene encoding GCaMP3, which is a calcium sensitive GFP that emits GFP fluorescence when bound to intracellular calcium, was introduced into a human iPS cell line (253G1) or a monkey iPS cell line (HT4M2) by AAVS1 region-specific gene transfer mediated by CRISPR. From the human GCaMP3-iPS cells, cardiomyocytes were induced in the same manner as in Section 1 to prepare an aggregate of cardiomyocytes that emitted GFP fluorescence in response to the change in intracellular calcium concentration during the beating. Also, from the monkey GCaMP-iPS cells, cardiomyocytes were induced using cytokines as described previously (Nat Biotechnol. 2007 September; 25(9): 1015-24. Epub 2007 Aug. 26) to prepare an aggregate of cardiomyocytes that emitted GFP fluorescence in response to the change in intracellular calcium concentration. Specifically, the monkey GCaMP-iPS cells were cultured for 24 hours with RPMI-B27 medium (Invitrogen) supplemented with human recombinant activin A (R&D Systems) (100 ng/ml), and then for four days with RPMI-B27 medium supplemented with human recombinant BMP4 (R&D Systems) (10 ng/ml). After the medium was replaced with RPMI-B27 medium without these cytokines, the cells were cultured for 21 days. The GCaMP-cardiomyocytes were dispersed into single cells with a trypsin/collagenase solution, and seeded on Sumilon PrimeSurface 96-well V-bottom plates at $1\times10^5$ cells/well to form uniform aggregates (700 to 1000 μm in diameter). The aggregates were used to analyze the change in intracellular calcium concentration wave, which synchronized the beating of cardiomyocytes.

Figure 3:
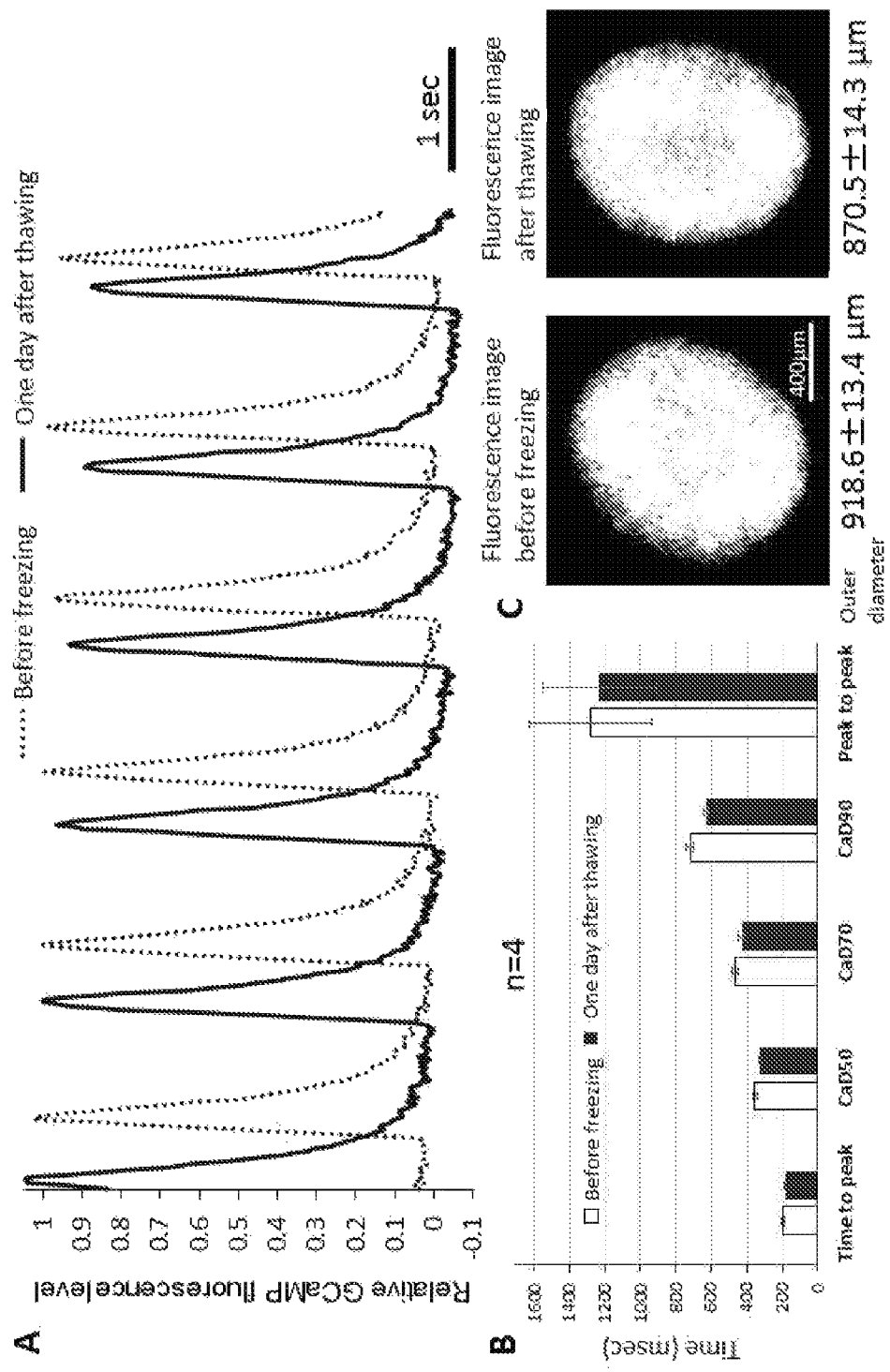
FIGS. 3A, 3B, and 3C show the change in fluorescence pattern of GCaMP-cardiomyocytes before and after freeze-thaw of cells frozen by aggregate freezing.

4. Change in Fluorescence Pattern of GCaMP-Cardiomyocytes Before and after Freeze-Thaw in Aggregate Freezing Using the aggregates of GCaMP-cardiomyocytes derived from human iPS cells, the wave pattern of intracellular calcium response was measured before freezing and one day after thawing (FIG. 3-A). There was no significant change in wave parameters (Time to peak (TtP), CAD50, 70, 90, as described in Section 6 hereinafter) and the beat interval (Peak-to peak (PtP)) before and after freeze-thaw (FIG. 3-B). The outer diameter of the aggregate was reduced by only about 5-10% and the aggregate maintained the basic shape after freeze-thaw (FIG. 3-C). These results demonstrate that the size and morphology as well as the pattern of electrophysiological responses were highly conserved before and after freeze-thaw.

Figure 4:
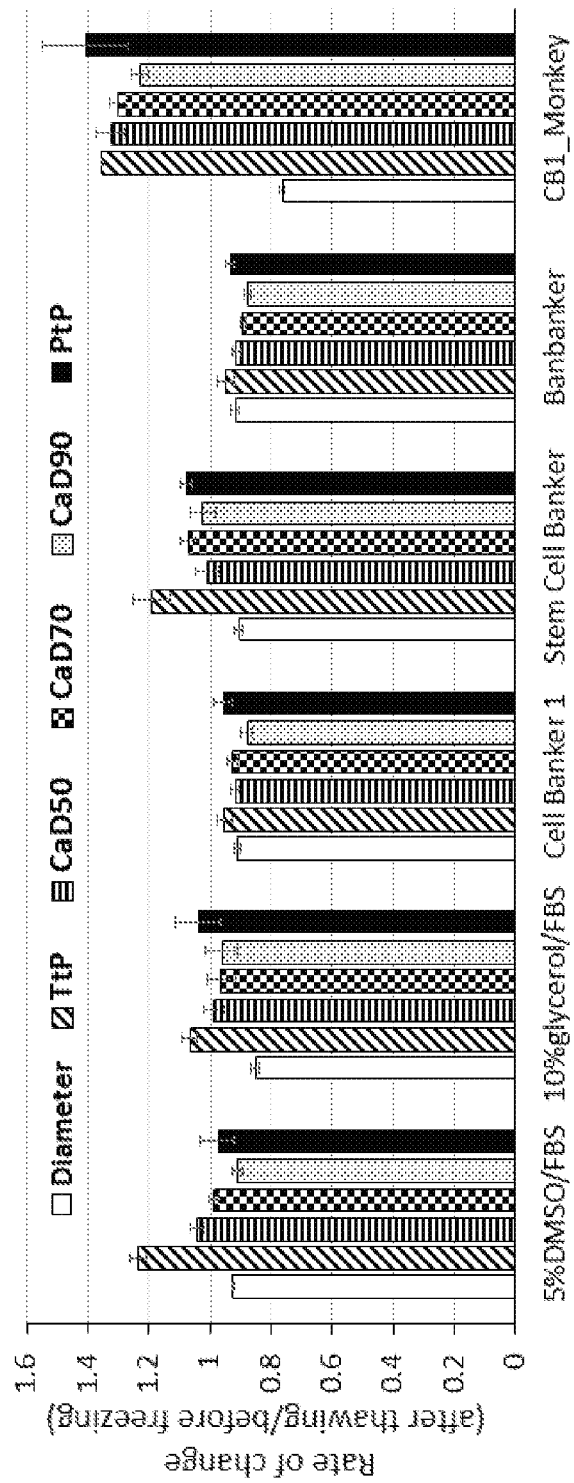
FIG. 4 shows the rate of change in parameters before and after freeze-thaw of human or monkey iPS-derived cardiomyocytes frozen by aggregate freezing and the comparison of cryoprotective solutions.

5. Rate of Change in Parameters Before and after Freeze-Thaw of Aggregates and Comparison of Cryoprotective Solutions In place of CELLBANKER 1 (Nippon Zenyaku Kogyo Co., Ltd.), 5% DMSO-containing fetal bovine serum (FBS) (5% DMSO/FBS solution) (DMSO (Sigma), FBS (Gibco)), 10% glycerol-containing bovine fetal serum (FBS) (10% glycerol/FBS solution) (glycerol (Sigma), FBS (Gibco)), STEM-CELLBANKER (Nippon Zenyaku Kogyo Co., Ltd.), or BAMBANKER (NIPPON Genetics Co, Ltd.) was used to freeze and thaw an aggregate of human iPS-derived cardiomyocytes in the same manner as in Section 1. To analyze the change before and after freezing, each parameter was measured before freezing and one day after thawing of the aggregate. Also, the monkey iPS-derived cardiomyocytes as described in Section 3 were frozen by aggregate freezing in the same manner as in Section 1 using CELLBANKER 1 as a cryoprotective solution to analyze the change before and after freezing. The outer diameter of aggregates of human iPS cell-derived cardiomyocytes (shown as "diameter" in FIG. 4) only reduced by about 10% with any of the cryoprotective solutions. Also, the rate of change in each parameter of GCaMP fluorescence wave (TtP, CaD50, 70, 90, PtP) before and after freezing was within ±25% and no significant change was observed. The diameter of aggregates of monkey iPS cell-derived cardiomyocytes reduced by about 20% and each parameter of GCaMP fluorescence wave increased by about 20-40%. The monkey iPS-derived cardiomyocytes induced by the method using cytokines were also applicable for freeze-thaw while maintaining functionality although the rate of change in monkey iPS-derived cardiomyocytes was greater than that in human iPS-derived cardiomyocytes.

Figure 5:
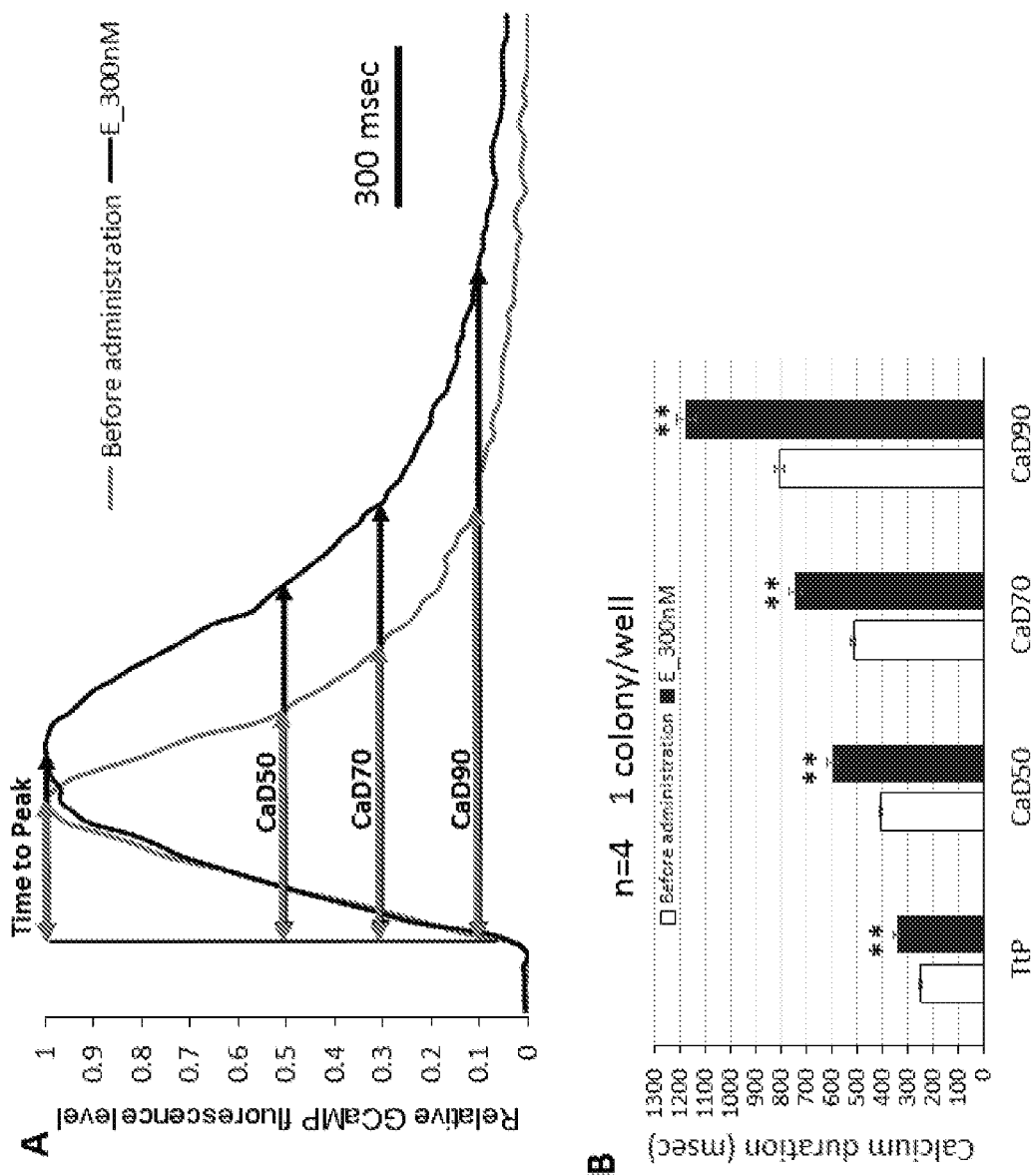
FIGS. 5A and 5B show the measurement of effect of E4031 on an aggregate of cardiomyocytes after freeze-thaw with GCaMP fluorescence.

6. Measurement of Effect of E4031 on Aggregates of Cardiomyocytes after Freeze-Thaw with GCaMP Fluorescence A HERG channel inhibitor E4031 (300 nM) was added to an aggregate of GCaMP-cardiomyocytes derived from human iPS cells seven days after thawing to compare parameters of GCaMP fluorescence wave (change in intracellular calcium ion concentration) before and 10 minutes after the E4031 addition. Analyzed were time from the rise to the peak of fluorescence wave (TtP), and time from the rise to the peak of fluorescence wave and then to the decrease to 50% of the peak value (CaD50), to 70% of the peak value (CaD70), or to 90% of the peak value (CaD90) (FIG. 5-A). All the parameters were extended around 40% due to the addition of E4031 and variation among wells was very small (FIG. 5-B). Inhibition of HERG channels was known to extend the duration of cardiac action potential and intracellular calcium ion increase, which is observed as drug-induced QT prolongation in the electrocardiogram. The results demonstrate that drug response to a HERG channel inhibitor (QT extension) is stably detected even after freeze-thaw.

Figure 6:
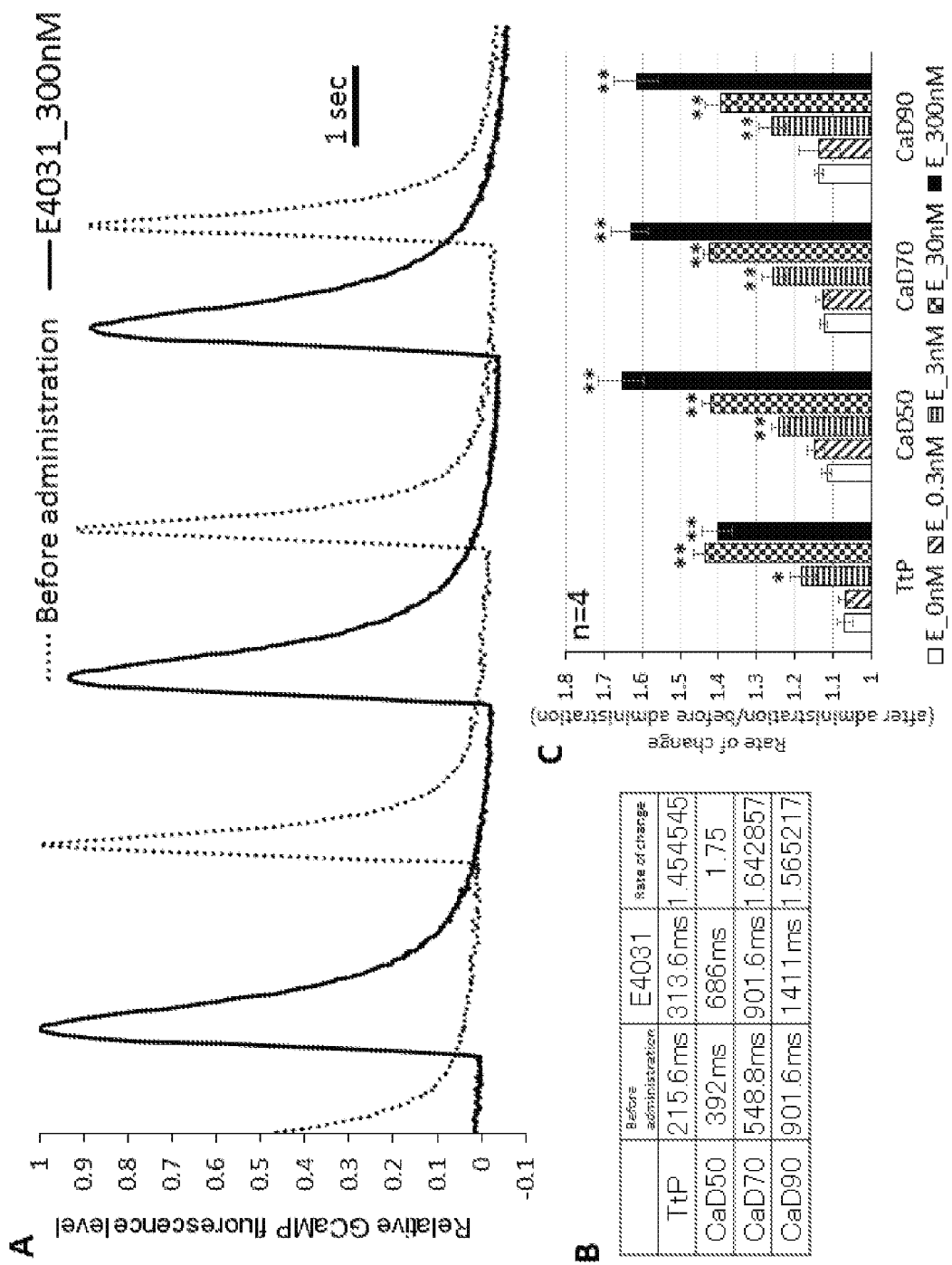
FIGS. 6A, 6B, and 6C show the concentration-dependent effect of E4031 on an aggregate of cardiomyocytes after freeze-thaw.

7. Concentration-Dependent Effect of E4031 on Aggregates of Cardiomyocytes after Freeze-Thaw E4031 was added to an aggregate of GCaMP-cardiomyocytes derived from human iPS cells seven days after thawing at 0, 0.3, 3, 30, or 300 nM to analyze the rate of change with E4031. The GCaMP fluorescence waves before and after the addition of 300 nM E4031 (FIG. 6-A) and the rate of change in wave parameters (FIG. 6-B) are shown. The values of TtP, CAD50, CAD70, and CAD90 were extended in a concentration-dependent manner with 3 nM or more E4031 (FIG. 6-C). The results demonstrate that drug response to a HERG channel inhibitor (QT extension) is stably detected with high sensitivity after freeze-thaw of aggregates. The concentration-dependent drug response to E4031 (QT extension) as shown herein is a useful characteristics for the evaluation of drug-induced cardiotoxicity. These results demonstrate that cardiotoxicity may be evaluated after freeze-thaw of aggregates.

Figure 7:
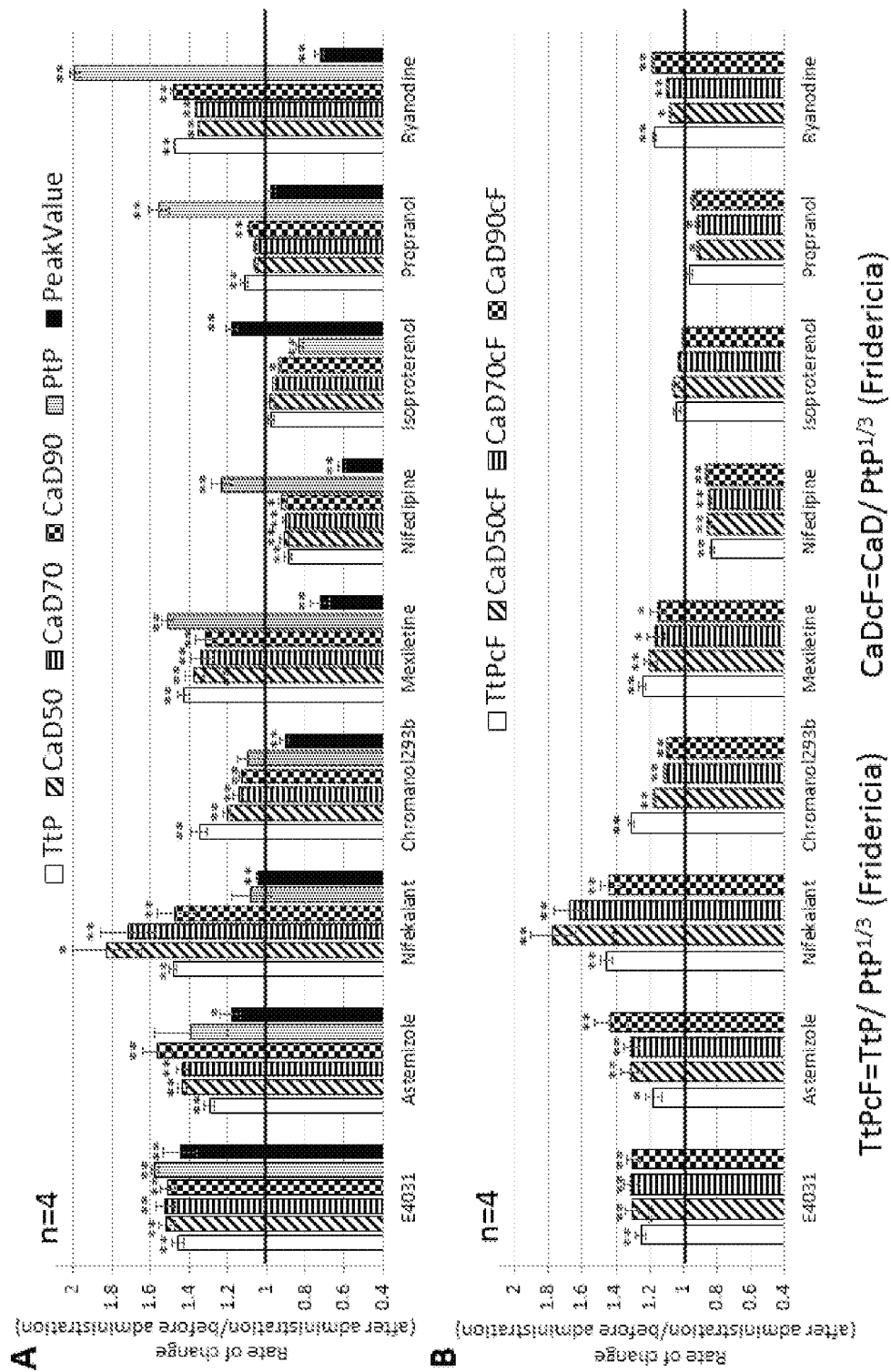
FIGS. 7A and 7B show the effects of some agents (E4031, astemizole, nifekalant, chromanole 293b, mexiletine, nifedipine, isoproterenol, propranol, ryanodine) on an aggregate of cardiomyocytes after freeze-thaw measured with GCaMP fluorescence.

8. Effects of Some Agents (E4031, Astemizole, Nifekalant, Chromanole 293b, Mexiletine, Nifedipine, Isoproterenol, Propranol, Ryanodine) on Aggregates of Cardiomyocytes after Freeze-Thaw To an aggregate of GCaMP-cardiomyocytes derived from human iPS cells seven days after thawing, 300 nM E4031, 1 μM astemizole, 1 μM nifekalant, 10 μM chromanole 293b, 30 μM mexiletine, 50 nM nifedipine, 300 nM isoproterenol, 1 μM propranol or 50 μM ryanodine was added, and the rate of change in each parameter was analyzed (FIG. 7-A). The rate of change in the corrected value obtained by dividing the value of TtP, CaD50, CAD70, or CAD90 by cube root of PtP (TtPcF, CaD50cF, CAD70cF, or CAD90cF) was also shown (FIG. 7-B). This correction has been used in analyzing drug-induced QT prolongation (QT corrected Fridericia). E4031, astemizole, and nifekalant are HERG channel inhibitors, chromanole 293b is a KCNQ1 channel inhibitor, mexiletine is a voltage-gated sodium channel inhibitor, nifedipine is an L-type calcium channel inhibitor, isoproterenol is a β stimulant, propranol is a β inhibitor, and ryanodine is an inhibitor of the endoplasmic reticulum ryanodine receptor. The HERG inhibitors, the KCNQ1 inhibitor, and the voltage-gated sodium channel inhibitor extended the values of TtP, CAD50, CAD70 and CAD90, and the L-type calcium channel inhibitor shortened these parameters. The β stimulant decreased PtP (increased heart rate); the β inhibitor increased PtP (decreased heart rate); the ryanodine receptor inhibitor increased PtP and decreased the peak value of GCaMP fluorescence (PeakValue, intracellular calcium increase). These results indicate that calcium response in aggregates of cardiomyocytes after freeze-thaw reflects the effects of various agents on actual cardiac myocytes.

Figure 8:
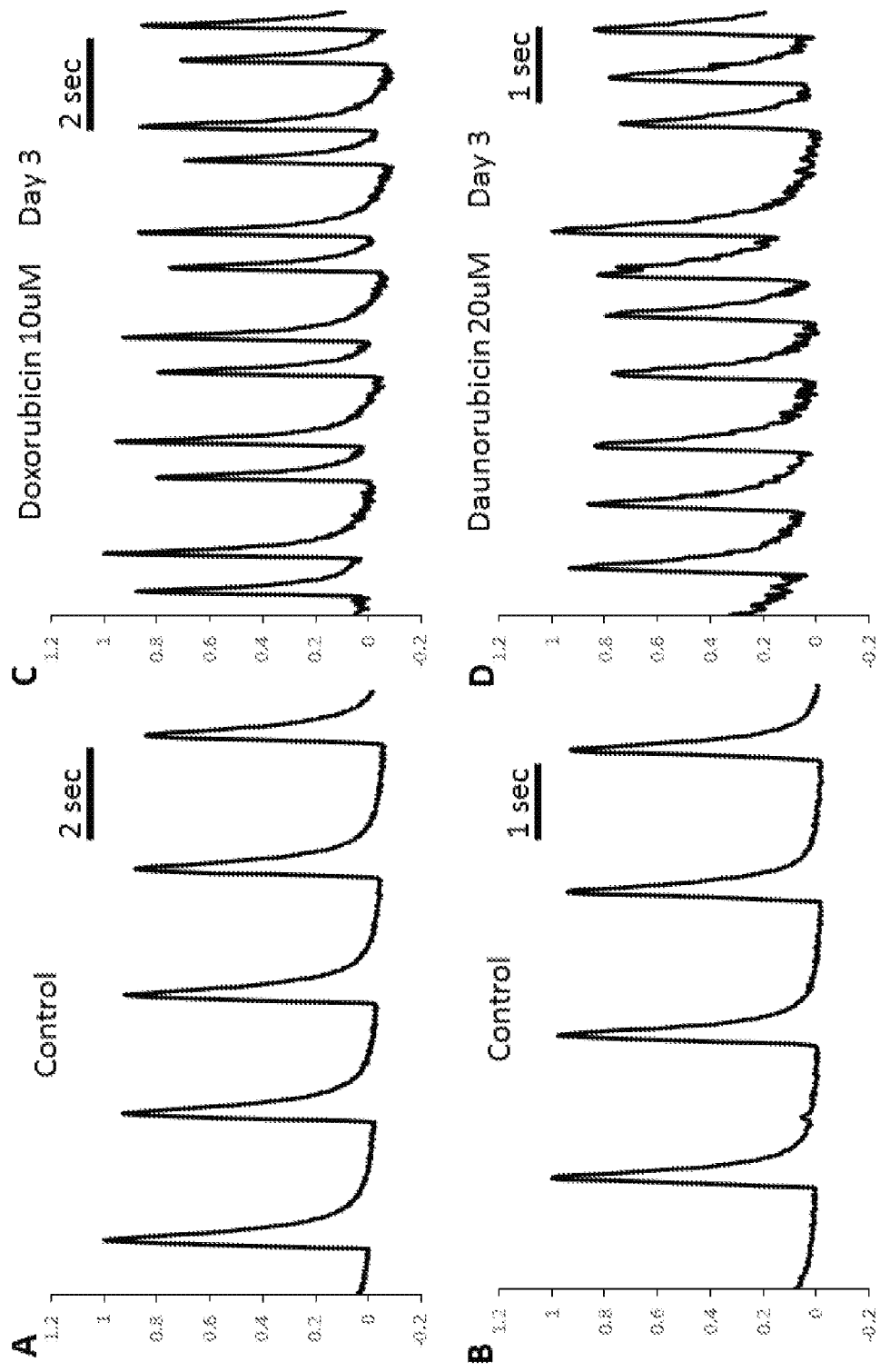
FIGS. 8A, 8B, 8C, and 8D show the cardiotoxicity of anthracycline in an aggregate of cardiomyocytes after freeze-thaw.

9. Cardiotoxicity of Anthracycline in Aggregates of Cardiomyocytes after Freeze-Thaw To detect cardiotoxicity of anthracycline anticancer agents, doxorubicin (10 µM) or daunorubicin (20 µM), was added for 24 hours to an aggregate of GCaMP-cardiomyocytes derived from human iPS cells seven days after thawing. The intracellular calcium wave was plotted with GCaMP fluorescence for an aggregate of cardiomyocytes without any agent (control) (FIGS. 8-A, 8-B), three days after the addition of doxorubicin (FIG. 8-C), or three days after the addition of daunorubicin (FIG. 8-D). The anthracycline-added aggregates showed short PtP, tachycardia, variable heartbeat interval, and arrhythmia (FIGS. 8-C, 8-D). The aggregate was demonstrated to be useful to detect not only short term cardiotoxicity seen in a several minutes to several tens of minutes, such as QT prolongation, but also long term cardiotoxicity seen in several days or more, such as cardiotoxicity with anti-cancer agents.

Figure 9:
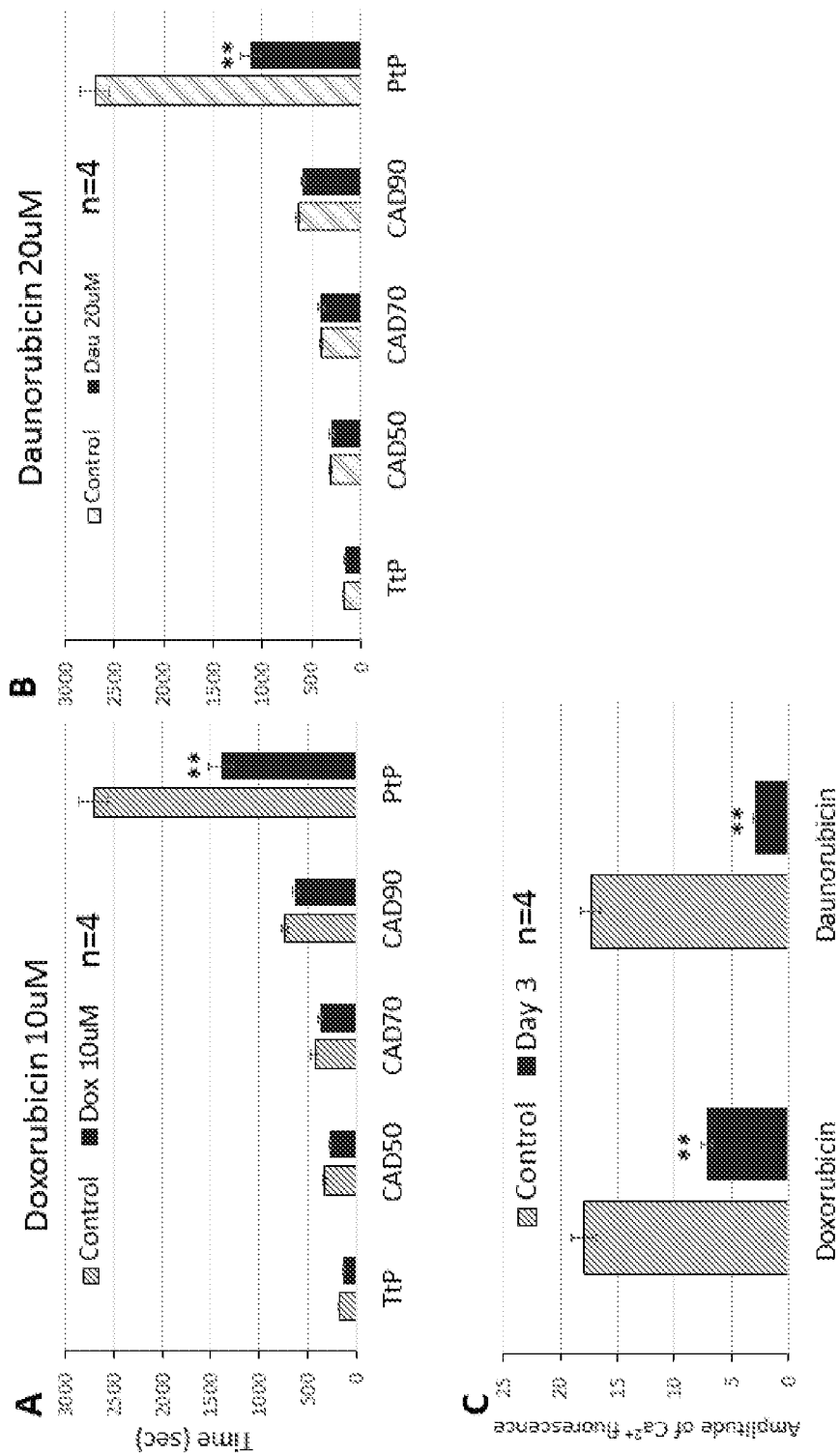
FIGS. 9A, 9B, and 9C show the analysis of cardiotoxicity of anthracycline in an aggregate of cardiomyocytes after freeze-thaw.

10. Analysis of Cardiotoxicity of Anthracycline in Aggregates of Cardiomyocytes after Freeze-Thaw The change in parameters of GCaMP fluorescence wave was analyzed with the addition of doxorubicin (10 µM) or daunorubicin (20 µM) (FIGS. 9-A, 9-B). Although TtP and CAD were not significantly changed, PtP significantly decreased and occurrence of tachycardia was quantitatively shown. In addition, the amplitude of GCaMP fluorescence wave (the absolute value of the amount of fluorescence from the rise to the peak) tended to decrease significantly (FIG. 9-C). These results suggest that cardiotoxicity of anthracycline induced myocardial cell death or decrease in intracellular calcium ion increase, resulting in tachycardia or arrhythmia.

Figure 10:
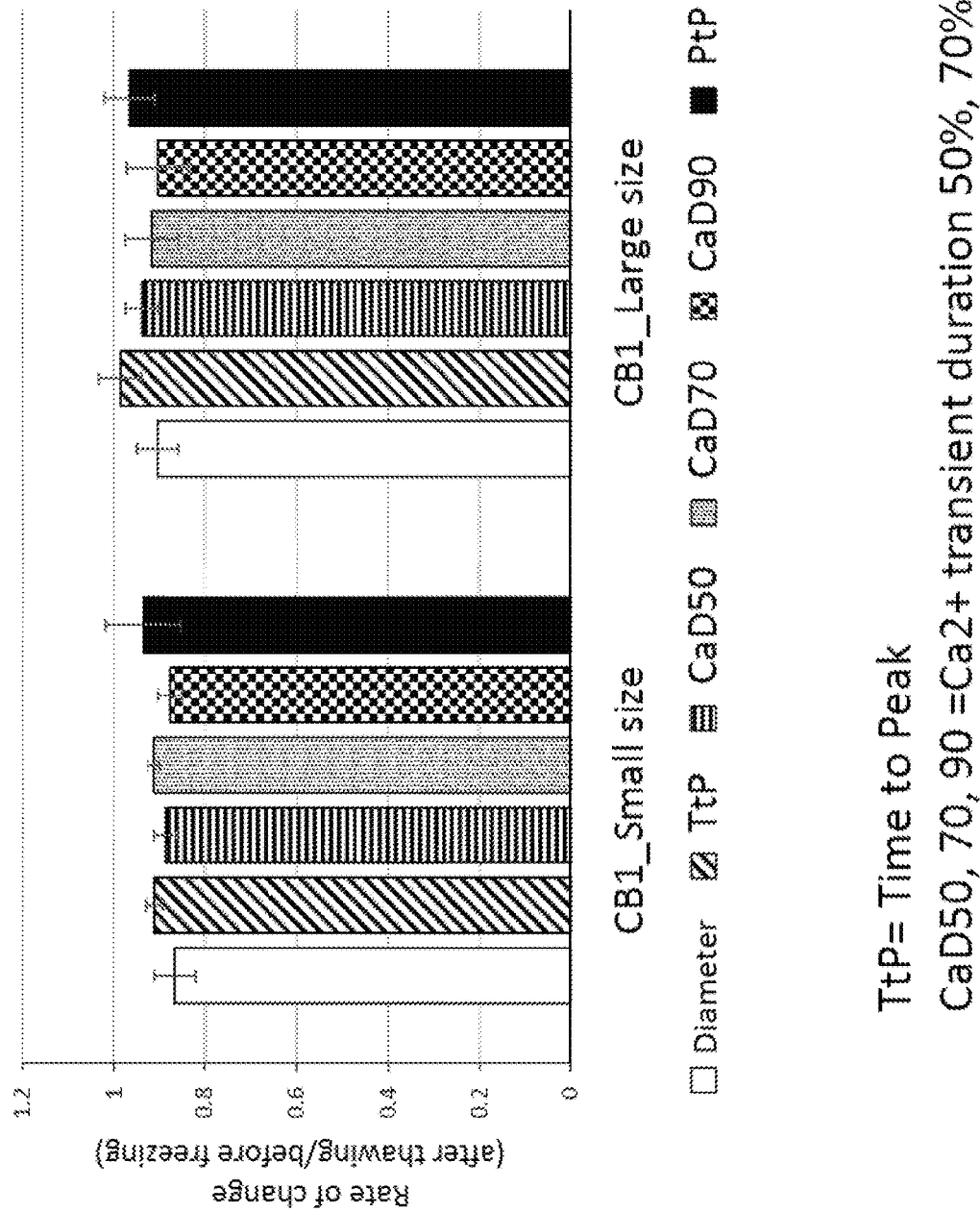
FIG. 10 shows the rate of change in parameters before and after freeze-thaw of aggregates in different sizes.

11. Rate of Change in Parameters Before and after Freeze-Thaw of Aggregates in Different Sizes The human iPS-derived cardiomyocytes described in Section 1 were used to analyze the change before and after freeze-thaw of an aggregate in a small size that was prepared from a relatively small number of cells ($0.1 \times 10^5$ cells/well) and had a diameter of 100 to 200 µm (CB1_Small size), and an aggregate in a large size that was prepared from a relatively large number of cells ($2 \times 10^5$ cells/well) and had a diameter of 1200 to 1600 µm (CB1_Large size). These aggregates were frozen by aggregate freezing using CELL-BANKER 1 as a cryoprotective solution in the same manner as in Section 1. Similar to the results in Section 5, the outer diameter of the aggregate in either size (shown as "diameter" in FIG. 10) decreased only about 10%. In addition, the rate of change in each parameter of GCaMP fluorescence wave (TtP, CaD50, 70, 90, PtP) before and after freezing was within ±25% and thus no significant change was observed. Aggregates formed from different number of cells and in different sizes were also applicable to the freeze-thaw.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of freezing an aggregate of pluripotent stem cell-derived cardiomyocytes, or preparing a frozen aggregate of pluripotent stem cell-derived cardiomyocytes, comprising:
   (i) immersing an aggregate of pluripotent stem cell-derived cardiomyocytes in a cryoprotective solution for 5 to 60 minutes at 2 to 24° C.; and
   (ii) freezing the aggregate immersed in the cryoprotective solution at −60 to −150° C.,
   wherein the aggregate has a diameter of 50 to 5000 µm;
   wherein the cardiomyocytes show a viability of 80% or more 3 days after the aggregate is thawed.

2. The method of claim 1, wherein the aggregate is immersed in the cryoprotective solution for 10 to 30 minutes.

3. The method of claim 1, wherein the aggregate is immersed in the cryoprotective solution at 2 to 10° C.

4. The method of claim 1, wherein the aggregate is frozen at −70 to −90° C.

5. The method of claim 1, wherein the aggregate has a diameter of 50 to 2000 µm.

6. The method of claim 1, wherein the pluripotent stem cell-derived cardiomyocytes express GFP-calmodulin-myosin light chain fragment-binding protein.

7. The method of claim 1, wherein the pluripotent stem cell-derived cardiomyocytes are cells obtained by the method comprising:
   (1) culturing pluripotent stem cells in a medium containing a WNT signaling activator and a PKC activator; and
   (2) culturing the cells obtained by the step (1) in a medium containing a WNT signaling inhibitor, a Src inhibitor, and an EGFR inhibitor.

8. The method of claim 1, wherein the cryoprotective solution comprises DMSO or glycerol.

* * * * *